US006709427B1

(12) United States Patent
Nash et al.

(10) Patent No.: US 6,709,427 B1
(45) Date of Patent: Mar. 23, 2004

(54) SYSTEMS AND METHODS FOR DELIVERING AGENTS INTO TARGETED TISSUE OF A LIVING BEING

(75) Inventors: John E. Nash, Chester Springs, PA (US); Douglas G. Evans, Downingtown, PA (US); David M. Hoganson, West Chester, PA (US)

(73) Assignee: Kensey Nash Corporation, Exton, PA (US)

( * ) Notice: Subject to any disclaimer, the term of this patent is extended or adjusted under 35 U.S.C. 154(b) by 0 days.

(21) Appl. No.: 09/368,410

(22) Filed: Aug. 5, 1999

(51) Int. Cl.$^7$ .............................................. A61M 31/00
(52) U.S. Cl. ...................................... 604/508; 604/511
(58) Field of Search ............................ 604/22, 500, 19, 604/21, 502, 506–508, 511, 57, 60, 93.01, 181; 606/159; 128/898; 424/400, 422–426, 489

(56) References Cited

U.S. PATENT DOCUMENTS

| | | | |
|---|---|---|---|
| 1,902,418 | A | 3/1933 | Pilgrim |
| 2,398,544 | A | 4/1946 | Lockhart |
| 2,737,946 | A | 3/1956 | Hein, Jr. |

(List continued on next page.)

6,261,585 B1 * 7/2001 Sefton et al. ............... 424/423

FOREIGN PATENT DOCUMENTS

| | | |
|---|---|---|
| DE | 296 19 029 U1 | 5/1997 |
| EP | 0 807 412 A1 | 11/1997 |
| EP | 0 876 803 A2 | 11/1998 |

(List continued on next page.)

OTHER PUBLICATIONS

Basic Fibroblast Growth Factor in a Porcine Model of Chronic Myocardial Ischemia: A comparison of Angiographic, Echocardiographic and Coronary Flow Parameters. Lopez et al., The Journal of Pharmacology and Experimental Therapeutics, vol. 282, No. 1, pp. 385–390, 1997.

(List continued on next page.)

Primary Examiner—Michael J. Hayes
(74) Attorney, Agent, or Firm—Caesar, Rivise, Bernstein, Cohen & Pokotilow, Ltd.

(57) ABSTRACT

The systems basically comprise a delivery system for accessing the targeted tissue within the living being and introduction of at least one agent at select locations in the into the myocardium and other select tissues. The delivery systems are arranged to access the tissues of the heart. One or more of the systems can be utilized during transluminal, transthoracic and direct surgical access procedures. Where appropriate, for example in the case of intraventricular access, portions of the system are steerable to properly orient the device. The instruments may pierce the heart tissue and create channels extending from the endocardium, the epicardium, or the cardiac vessels. When tissue penetration is utilized, the device may include a feature to control the depth of penetration. To minimize bleeding through the channels the device can dilate small initial punctures that later contract down after device removal. When the formation of channels is required, this can be achieved, by way of example, with a rotary-tipped device, pressurized fluid jet devices, vibratory instruments and piercing needle-like tip devices. The system may utilize some form of mechanical action or application of energy (e.g. electrical, sonic, thermal, optical, pressurized fluid, radio frequency (RF), nuclear) in the process. The mechanical action or energy application may affect the surroundings tissues at a distance from the device. The agent delivered to the tissue may include one or more of pharmaceuticals, biologically active agents, radiopaque materials, etc.

5 Claims, 20 Drawing Sheets

US 6,709,427 B1

Page 2

U.S. PATENT DOCUMENTS

| | | | | |
|---|---|---|---|---|
| 2,762,370 A | | 9/1956 | Venditty | |
| 2,800,903 A | | 7/1957 | Smoot | |
| 3,815,594 A | | 6/1974 | Doherty | |
| 3,887,699 A | | 6/1975 | Yolles | |
| 3,930,505 A | | 1/1976 | Wallach | |
| 4,165,739 A | | 8/1979 | Doherty et al. | |
| 4,315,742 A | | 2/1982 | Nash et al. | |
| 4,406,656 A | | 9/1983 | Hattler et al. | |
| 4,589,412 A | | 5/1986 | Kensey | |
| 4,631,052 A | | 12/1986 | Kensey | |
| 4,637,905 A | | 1/1987 | Gardner | |
| 4,652,441 A | | 3/1987 | Okada et al. | |
| 4,658,817 A | | 4/1987 | Hardy | |
| 4,664,112 A | | 5/1987 | Kensey et al. | |
| 4,679,558 A | | 7/1987 | Kensey et al. | |
| 4,686,982 A | | 8/1987 | Nash | |
| 4,690,672 A | | 9/1987 | Veltrup | |
| 4,700,705 A | | 10/1987 | Kensey et al. | |
| 4,747,406 A | | 5/1988 | Nash | |
| 4,747,821 A | | 5/1988 | Kensey et al. | |
| 4,749,376 A | | 6/1988 | Kensey et al. | |
| 4,790,813 A | | 12/1988 | Kensey | |
| 4,795,438 A | | 1/1989 | Kensey et al. | |
| 4,839,215 A | | 6/1989 | Starling et al. | 428/131 |
| 4,900,303 A | | 2/1990 | Lemelson | 604/54 |
| 4,994,033 A | | 2/1991 | Shockey et al. | |
| 5,021,044 A | | 6/1991 | Sharkawy | |
| 5,037,432 A | | 8/1991 | Molinari | |
| 5,042,984 A | | 8/1991 | Kensey et al. | |
| 5,087,244 A | | 2/1992 | Wolinsky et al. | |
| 5,112,305 A | | 5/1992 | Barath et al. | |
| 5,199,951 A | | 4/1993 | Spears | |
| 5,244,460 A | | 9/1993 | Unger et al. | |
| 5,279,565 A | | 1/1994 | Klein et al. | |
| 5,288,502 A | | 2/1994 | McGinity et al. | |
| 5,415,636 A | * | 5/1995 | Forman | 604/101.03 |
| 5,415,637 A | | 5/1995 | Khosravi | |
| 5,456,667 A | | 10/1995 | Ham et al. | |
| 5,496,267 A | | 3/1996 | Drasler et al. | |
| 5,498,238 A | | 3/1996 | Shapland et al. | |
| 5,527,292 A | | 6/1996 | Adams et al. | |
| 5,591,159 A | | 1/1997 | Taheri | |
| 5,607,421 A | | 3/1997 | Jeevanandam et al. | |
| 5,655,548 A | | 8/1997 | Nelson et al. | |
| 5,674,197 A | | 10/1997 | van Muiden et al. | |
| 5,704,911 A | | 1/1998 | Parsons | |
| 5,718,921 A | | 2/1998 | Mathiowitz et al. | |
| 5,755,682 A | | 5/1998 | Knudson et al. | |
| 5,810,836 A | | 9/1998 | Hussein et al. | |
| 5,836,905 A | * | 11/1998 | Lemelson et al. | 604/101.05 |
| 5,840,059 A | | 11/1998 | March et al. | 604/53 |
| 5,871,469 A | | 2/1999 | Eggers et al. | |
| 5,878,751 A | | 3/1999 | Hussein et al. | 128/898 |
| 5,879,713 A | | 3/1999 | Roth et al. | 424/489 |
| 5,893,840 A | | 4/1999 | Hull et al. | 604/96 |
| 5,904,670 A | | 5/1999 | Schreiner | 604/280 |
| 5,912,017 A | | 6/1999 | Mathiowitz et al. | |
| 5,925,016 A | | 7/1999 | Chornenky et al. | |
| 5,935,119 A | | 8/1999 | Guy et al. | 604/500 |
| 5,941,868 A | | 8/1999 | Kaplan et al. | |
| 5,997,525 A | | 12/1999 | March et al. | 604/508 |
| 6,080,170 A | * | 6/2000 | Nash et al. | 606/159 |

FOREIGN PATENT DOCUMENTS

| | | |
|---|---|---|
| WO | WO 97/32551 | 9/1997 |
| WO | WO 99/22658 | 3/1998 |
| WO | WO 98/19614 | 5/1998 |
| WO | WO 98/39038 | 9/1998 |
| WO | WO 98/49964 | 11/1998 |
| WO | WO 99/27985 | 11/1998 |
| WO | WO 99/44523 | 3/1999 |
| WO | WO 99/44524 | 3/1999 |
| WO | WO 99/22655 | 5/1999 |
| WO | WO 99/33510 | 7/1999 |

OTHER PUBLICATIONS

Basic FGF Enhances Endothelium–Dependent Relaxation of the Collateral–Perfused Coronary Microcirculation. Sellke et al., The American Physiological Society, 1994, pp. H1303–H1311.

Sellke et al., Therapeutic Angiogenesis With Basic Fibroblast Growth Factor: Technique and Early Results, Ann Thorac. Surg., 1540–1544, 1998.

Sen et al., Transmyocardial Acupuncture: A New Approach To Myocardial Revascularization, Journal of Thoracic and Cardiovascular Surgery, 50:181–187, Aug. 1965.

Moosdorf, et al., Transmyocardial Laser Revascularization– Morphologic Pathophysiologic And Historical Principles Of Indirect Revascularization Of The Heart Muscle, Z Kardiol, 86(3): 147–164, Mar. 1997.

Wintzer et al., Transmyocardial Laser Revascularization. Historical Features In Human Nonresponder Myocardium appearing in Circulation, 95(c): 371–375, Jan. 21, 1997.

Massimo et al., Myocardial Revascularization By A New Method Of Carrying Blood Directly From The Left Ventricular Cavity Into The Coronary Circulation, J. Thorac. Surg., 34:257–264, Aug. 1957.

Pifarre, et al., Myocardial Revascularization by Transmyocardial Acupuncture, A Physiologic Impossibility, The Journal of Thoracic and Cardiovascular Surgery, 58:424–431, 1969.

Mirhoseini, et al., New Concepts in Revascularization of the Myocardium, Ann. Thor. Surg., 45:415–420, Apr. 1988.

Sanborn, et al., Abstract of Percutaneous Endocardial Gene Therapy in Vivo Gene Transfer and Expression. The Journal of the American College of Cardiology, 33:262A, Feb. 1999.

Edelman et al., Perivascular and Intravenous Administration Of Basic Fibroblast Growth Factor: Vascular And Solid Organ Deposition, Proc. Natl. Acad. Sci., USA, vol. 90, 1513–1517, Feb. 1993.

Taguchi et al., Preparation Of A Novel Functional Hydrogel Consisting Of Sulfated Glucoside–bearing Polymer: Activation Of Basic Fibroblast Growth Factor, 386–391.

Arras et al., The Delivery Of Angiogenic Factors To The Heart By Microsphere Therapy, Nature Biotechnology, vol. 16, 159–162, Feb. 1998.

Kimura et al., Cellular Response in Subretinal Neovascularization Induced By bFGF–Impregnated Microspheres, IOVS, Feb. 1999, vol. 40, 524–528.

Wilensky et al., Direct Intraarterial Wall Injection Of Microparticles Via A Catheter: A Potential Drug Delivery Strategy Following Angioplasty, American Heart Journal, vol. 122, 1136–1140, Oct. 1991.

Goldman et al., Experimental Method For Producing A Collageral Circulation To The Heart Directly From the Left Ventricle, The Journal of Thoracic and Cardiovascular Surgery, 31:364–374, 1965.

Fasol et al., Experimental Use Of A Modified Fibrin Glue To Induce Site–Directed Angiogenesis From The Aorta To The Heart, The Journal of Thoracic and Cardiovascular Surgery, vol. 107, 1432–1439, Jun. 1994.

Krabatash et al., Histological Findings After Transmyocardial Laser Revascularization, The Journal of Cardiac Surgery, 11:326–331, 1996.

Tabata et al., In Vitro Sorption and Desorption of Basic Fibroblast Growth Factor From Biodegradable Hydrogels, Biomaterials 19 (1988) 1781–1789.

Raoul Bonan, M.D, Local Drug Delivery for the Treatment of Thrombus and Restenosis, The Journal of Invasive Cardiology, 8:399–408, Oct. 1996.

Pelletier, et al., Angiogenesis and Growth Factor Expression in a Model of Transmyocardial Revascularization, Annuals of Thoracic Surgery, 66:12–18, 1998.

Uchida et al., Angiogenic Therapy of Acute Myocardial Infarction by Intrapericardial Injection of Basic Fibroblast Growth Factor and Heparin Sulfate: An Experimental Study, the American Heart Journal, 130:1182–1188, Dec. 1995.

Edelman, et al., Basic Fibroblast Growth Factor Enhances The Coupling Of Intimal Hyperplasia And Proliferation Of Vasa Vasorum in Injured Rat Arteries, J. Clin. Invest, vol. 89, Feb. 1992, 465–473.

Nishi et al, Basic Fibroblast Growth Factor Impregnated Hydrogel Microspheres For Embolization of Cerebral Arteriovenous Malformations, ASAIO Journal, 1998, M405–M410.

Harada, et al., Basic Fibroblast Growth Factor Improves Myocardial Function in Chronically Ischemic Porcine Hearts, J. Clin. Invest, vol. 94, Aug. 1994, 623–630.

Mack et al., Biologic Bypass with the Use of Adenovirus–Mediated Gene Transfer of the Complementary Deoxyribonucleic Acid for Vascular Endothelial Growth Factor 121 Improves Myocardial Perfusion and Function in the Ischemic Porcine Heart, The Journal of Thoracic and Cardiovascular Surgery, 115:168–177, Jan. 1998.

* cited by examiner

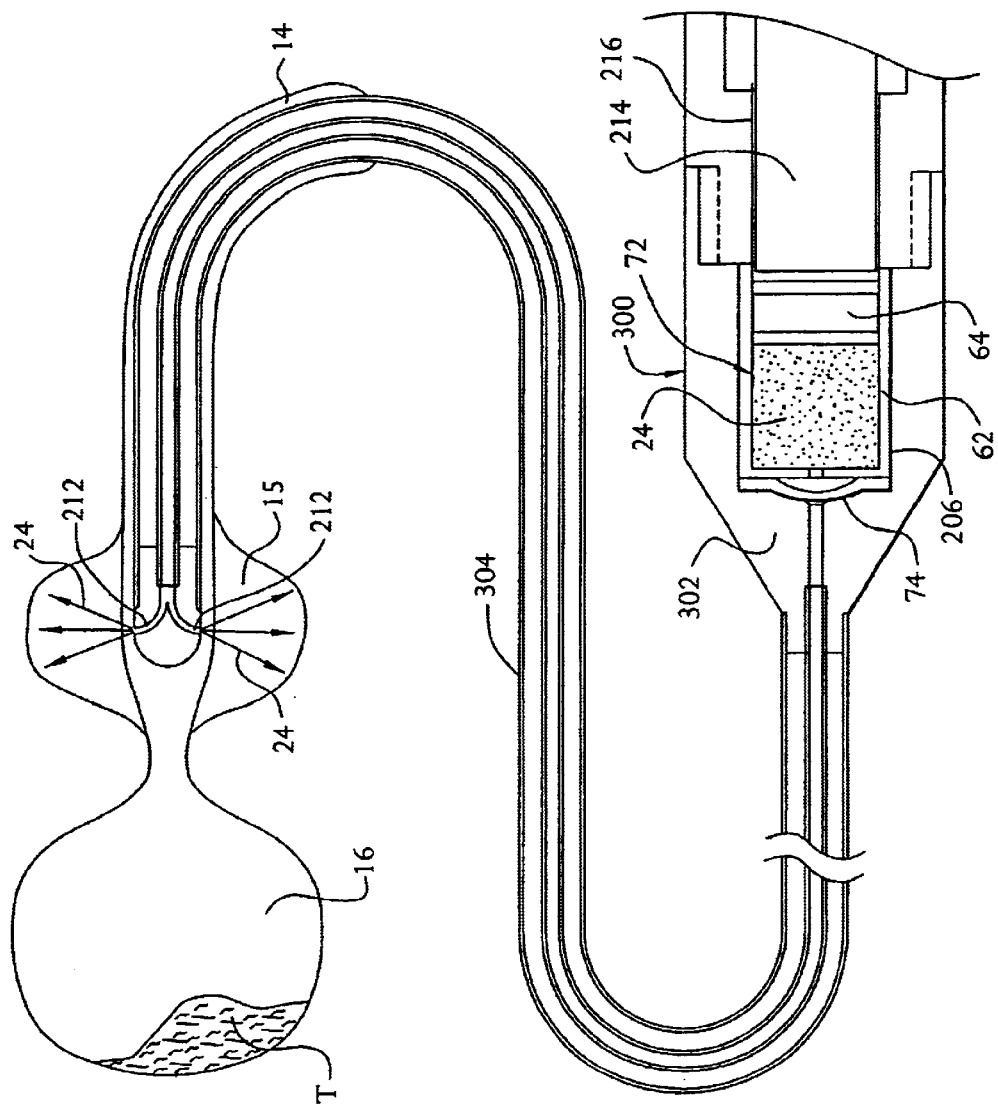

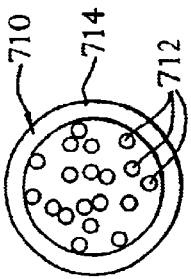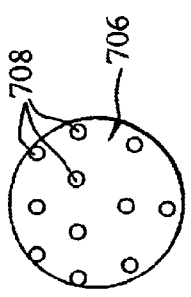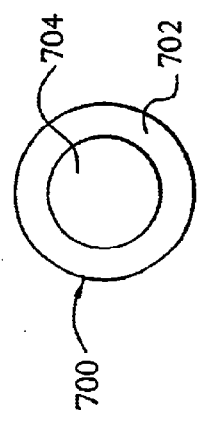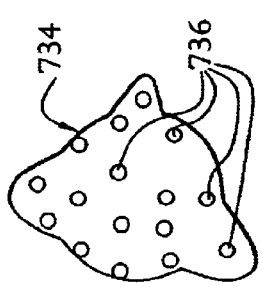

SYSTEMS AND METHODS FOR DELIVERING AGENTS INTO TARGETED TISSUE OF A LIVING BEING

BACKGROUND OF THE INVENTION

This invention relates generally to medical systems and procedures and more particularly to systems and procedures for delivering a flowable treatment agent into targeted tissues, e.g., cardiac tissue, of a living being.

Cardiovascular disease is the leading cause of death in the industrial world today. During the disease process, atherosclerotic plaques develop at various locations within the arterial system of those affected. These plaques restrict the flow of blood through the affected vessels. Of particular concern is when these plaques develop within the blood vessels that feed the muscles and other tissues of the heart. In healthy hearts, cardiac blood perfusion results from the two coronary arterial vessels, the left and right coronary arteries that perfuse the myocardium from the epicardial surface inward towards the endocardium. The blood flows through the capillary system into the coronary veins and into the right atrium via the coronary sinus. When atherosclerosis occurs within the arteries of the heart it leads to myocardial infarctions, or heart attacks, and ischemia due to reduced blood flow to the heart tissues. Over the past few years numerous devices and methods have been evaluated for treating cardiovascular disease, and for treating the resulting detrimental effects that the disease has upon the myocardium and the other heart tissues. They are: traditional surgical methods (e.g. open heart surgery), minimally invasive surgery, traditional interventional cardiology (e.g. angioplasty, atherectomy, stents), and advanced interventional cardiology (e.g. catheter based drug delivery). Other recent advances in cardiovascular disease treatment involve transmyocardial revascularization (TMR), and growth factor and gene delivery.

Traditional methods for treating cardiovascular disease utilize open surgical procedures to access the heart and bypass blockages in the coronary blood vessels. These procedures require an incision in the skin extending from the supra-sternal notch to the zyphoid process, the sawing of the sternum longitudinally in half, and the spreading of the rib-cage to surgically expose the patient's heart. Based upon the degree of coronary artery disease, a single, double, triple, or even greater number of vessels are bypassed. Each bypass is typically performed by creating a separate conduit from the aorta to a stenosed coronary artery at a location distal to the occluded site. In general, the conduits are either synthetic or natural bypass grafts. Grafting with the internal thoracic (internal mammary) artery directly to the blocked coronary site has been particularly successful with superior long-term patency results. During conventional cardiac surgery, the heart is stopped using cardioplegia solutions and the patient is put on cardiopulmonary bypass. The bypass procedure uses a heart-lung machine to maintain circulation throughout the body during the surgical procedure. A state of hypothermia may be induced in the heart tissue during the bypass procedure to preserve the tissue from necrosis. Once the procedure is complete, the heart is resuscitated and the patient is removed from bypass.

There are great risks associated with these traditional surgical procedures such as significant pain, extended rehabilitation time and high risk of mortality for the patient. The procedure is time-consuming and costly to perform. Traditional cardiac surgery also requires that the patient have both adequate lung and kidney function in order to tolerate the circulatory bypass associated with the procedure and a number of patients which are medically unstable are thus not a candidate for bypass surgery. As a result, over the past few years, minimally invasive techniques for performing bypass surgery have been developed and in some instances the need for cardiopulmonary bypass and extended recovery times are avoided. A number of companies, e.g., Heartport, Inc. of Redwood City, Calif. and Cardiothoracic Systems, Inc. of Cupertino, Calif., have developed devices that allow for cardiac surgical procedures that do not require a grossly invasive median sternotomy or traditional cardiopulmonary bypass equipment. The procedures result in a significant reduction in pain and rehabilitation time.

In addition, as an alternative to surgical methods, traditional interventional cardiology methods (e.g. angioplasty, atherectomy, and stents) non-surgical procedures, such as percutaneous transluminal coronary angioplasty (PTCA), rotational atherectomy, and stenting have been successfully used to treat this disease in a less invasive non-surgical fashion. In balloon angioplasty a long, thin catheter having a tiny inflatable balloon at its distal end is threaded through the cardiovascular system until the balloon is located at the location of the narrowed blood vessel. The balloon is then inflated to separate and expand the obstructing plaque and expand the arterial wall, thereby restoring or improving the flow of blood to the local and distal tissues. Rotational atherectomy utilizes a similarly long and thin catheter, but with a rotational cutting tip at its distal end for cutting through the occluding material. Stenting utilizes a balloon tipped catheter to expand a small coil-spring-like scaffold at the site of the blockage to hold the blood vessel open.

While many patients are successfully relieved of their symptoms and pain with traditional interventional procedures, in a significant number of patients the blood vessels eventually restenose or reocclude within a relatively short period of time. As such, researchers have explored advanced interventional cardiology methods (e.g., catheter based drug delivery, radiation therapy, etc.) to delay or prohibit the process of restenosis. As summarized by Raoul Bonan, MD. ("Local Drug Delivery for the Treatment of Thrombus and Restenosis, IAGS Proceedings, The Journal of Invasive Cardiology, 8:399–408, October 1996), the cardiology community has recently begun to augment standard catheter-based treatment techniques with devices that provide local delivery of medications to the treated site. This localized administration of drugs has shown promise for counteracting clotting, reducing inflammatory responses, and blocking proliferative responses.

Several devices are reported to be under evaluation for site specific drug delivery, such as the so-called "Channel Balloon" catheter of Boston Scientific (Natick, Mass.), the "Infiltrator" device of InterVentional Technologies (San Diego, Calif.), the "InfusaSleeve" device of LocalMed Inc. (Sunnyvale, Calif.), the "Dispatch" catheter of SciMed/Boston Scientific (Natick, Mass.), and an ultrasound enhanced catheter of EKOS (Bothell Wash.). The "Channel Balloon" catheter is an over-the-wire catheter with separated ports for balloon inflation and drug infusion. The "Infiltrator" device utilizes nipples in a balloon to force a drug into vessel wall.

U.S. Pat. No. 5,279,565 (Klein et al.) discloses a device for infusing a treatment site with a medicinal agent. The device has a flexible body and deflectable support frames that are deployed radially against the intended treatment site. The InfusaSleeve device of LocalMed, Inc. slides over existing balloons to position drug delivery ports against the artery wall. The Dispatch is an over the wire catheter with separate ports for drug infusion and balloon inflation.

U.S. Pat. No. 5,527,292 (Adams et al.) describes an intravascular device having an elongated flexible tube sized for insertion into a coronary vessel beyond a distal end of a guide catheter. In certain applications, the intravascular device is used as a drug (or other fluid) delivery device or as an aspiration device. In other applications, the intravascular device is used as a guiding means for placement of an angioplasty device, such as a guide wire or a balloon catheter. EKOS (Bothell, Wash.) has developed a site-specific catheter that uses ultrasound energy to enhance the performance of a thrombolytic drug. The ultrasound energy transports the drug molecules into the strands of fibrin bundles to dissolve clots more effectively than drugs alone. Several other drug delivery catheters have been described.

Balloon-tipped catheters, appropriate for drug delivery procedures, are also described in U.S. Pat. No. 5,087,244 (Wolinsky et al.). In particular, this patent describes a catheter having a balloon near its distal end is expanded with a medication that then flows through minute holes in the balloon surface at a low flow rate. The catheter pressurizes the medication so that it can be perfused at a controlled low flow rate to penetrate into the wall of the localized tissue.

U.S. Pat. No. 5,021,044 (Sharkawy) describes an intravascular treatment apparatus having a plurality of holes on the outer surface of the catheter body through which a drug may be delivered to a site within a vessel.

U.S. Pat. No. 5,112,305 (Barath et al.) describes a catheter for delivery of therapeutic chemical agents to an interior wall of a vessel, the catheter having a balloon near its distal end with tubular extensions projecting from its outer surface. The catheter is pressurized with a drug, which causes the balloon to expand. The drug then flows throughout the tubular extension into the vessel wall.

U.S. Pat. No. 4,406,656 (Hattler et al.) describes a collapsible multi-lumen venous catheter that can be used for drug injection.

U.S. Pat. No. 5,498,238 (Shapland et al.) discloses a method of simultaneous angioplasty and drug delivery to a localized portion of coronary or peripheral arteries or any other type of body passage that has a stricture. The drug delivery device is first positioned in a body passageway. The device is expanded in order to dilate the passage while simultaneously causing a selected drug to be transported across a drug transport wall of the device for direct contact with the passageway wall.

U.S. Pat. No. 5,415,637 (Khosravi) describes an intravascular catheter that is capable of delivering a drug, that is in the form of an already mixed solution or in the form of pellets, both intraluminally and endoluminally to an artery.

U.S. Pat. No. 5,199,951 (Spears) describes a method for treating a lesion in an artery by bonding a bioprotective material to the arterial wall with thermal energy to provide localized drug delivery. The device can use drugs that are trapped within microspheres that can be thermally bonded to tissues.

U.S. Pat. No. 4,994,033 (Shockey et al.) describes an intravascular treatment apparatus having a pair of expansion members concentrically arranged near its distal end wherein a drug is delivered to the outer expansion member. The expansion member expands against the vessel wall forcing the drug through minute holes in the outer member to bathe the vessel wall.

U.S. Pat. No. 5,456,667 (Ham et al.) describes an intravascular catheter with an expandable region formed of a tubular material at the distal end of the catheter body in a one-piece configuration and is radially expanded and contracted by means of a control wire. The interior of the expandable region is in fluid communication with a lumen in the catheter body to allow the delivery of a fluid to the artery via openings in the surface of the expandable region. The catheter is particularly adapted to hold open an artery after a vascular procedure such as a balloon angioplasty, and if desired to introduce a therapeutic drug or other fluid to the site of the vascular procedure.

The assignee of this present invention is also the assignee of previously described catheter-based devices for the local delivery of drugs into the arterial system. See for example, U.S. Pat. No. 4,589,412 (Kensey) and U.S. Pat. No. 4,631,052 (Kensey) disclose atherectomy catheters that utilize a cutting tip that is driven by the application of fluid pressure. As described, the catheters can be used to deliver drugs, oxygen, nitrates, calcium channel blockers or contrast media through the catheter tip into the arterial lumen.

U.S. Pat. No. 4,747,406 (Nash) and U.S. Pat. No. 4,686,982 (Nash), which are assigned to the same assignee as this invention, describe recanalization catheters with a high speed working end that is driven by a flexible drive shaft mounted within a bearing. The specification describes the use of fluid to cool and lubricate the catheter, as well as reduce the incidence of snagging as a result of the positive pressure applied to the artery wall. The fluid can include nitrates, drugs, or contrast media.

U.S. Pat. No. 4,664,112 (Kensey), U.S. Pat. No. 4,679,558 (Kensey et al.), and U.S. Pat. No. 4,700,705 (Kensey), assigned to the same assignee as this invention, describe small diameter catheter devices with a high-speed working head used for dilating lumens and stopping arterial or other lumen spasm. The specifications describe the use of fluids to cool and lubricate the catheter. The fluid can carry contrast media or drugs. The catheters may be useful for opening restrictions in lumens by bombarding the restriction with propelled fluids at high pressure which may force the liquid into the lumen walls by increasing the local dynamic or hydrostatic pressure induced by the injected liquid or the moving working head.

U.S. Pat. No. 4,790,813 (Kensey), also assigned to the same assignee as this invention, describes an atherectomy catheter that utilizes a cutting tip that is driven by the application of fluid pressure. As described, that catheter has the potential for the delivery of drugs, oxygen, nitrates, calcium channel blockers or contrast media through the catheter tip into the arterial lumen.

U.S. Pat. No. 4,795,438 (Kensey et al.), also assigned to the same assignee as this invention, describes a flexible small diameter catheter for effecting the formation of a restriction in a vessel. The patent teaches of a rotary catheter that is used to deliver fluid, particles, sclerosing liquid, micron-sized particles, and adhesive agents. In one aspect of the invention, the particles are embedded into the tissue contiguous with the working head of the catheter. The embedded particles cause the tissue to change, e.g. form scar tissue, whereupon a restriction is formed. Another aspect of the invention describes the use of abrasive particles to sclerose or abrade tissue.

U.S. Pat. No. 4,749,376 (Kensey et al.), U.S. Pat. No. 5,042,984 (Kensey et al.), and U.S. Pat. No. 4,747,821 (Kensey et al.), all assigned to the same assignee of this invention, describe drive-wire driven rotary catheters for opening an arterial restriction. The devices utilize the rotation of a working head to cause fluid to be thrown radially outward from the working head to impact the artery wall.

In general, these previous devices are suited to deliver drugs and other therapeutic agents locally to the immediate lumen (e.g., artery) wall to address restenosis. However, they do not address the problem of treating other heart tissues (e.g., myocardium) located beyond the arterial wall.

It has been shown that some patients can receive significant benefits from recently developed medical treatments. Some of these treatments are applied to other tissues of the heart (e.g. the myocardium). In addition, although the non-surgical interventional cardiology procedures are much less costly and less traumatic to the patient than traditional coronary bypass surgery, there are a number of patients for which these procedures are not suitable. For certain types of patients the presence of extremely diffuse stenotic lesions and total occlusion in tortuous vessels prohibits them from being candidates for traditional cardiac surgery. For these patients, direct myocardial revascularization has been performed by inducing the creation of new channels, other than the coronary arteries themselves, which are designed to supply oxygenated blood and remove waste products from the heart tissue (e.g. myocardium). Myocardial revascularization is a technique that was conceived to supplement the blood supply delivered to the heart by providing the ischemic inner surface of the heart, known as the endocardium, with direct access to the blood within the ventricular chamber. Typically the endocardium receives its nutrient blood supply entirely from the coronary arteries that branch through the heart wall from the outer surface known as the epicardium.

Needle acupuncture approaches to direct myocardial revascularization have been made and were based upon the premise that the heart of reptiles achieve myocardial perfusion via small channels between the left ventricle and the coronary arterial tree as described by Sen et al. in their article entitled "Transmyocardial Acupuncture: A New Approach To Myocardial Revascularization" in the Journal of Thoracic and Cardiovascular Surgery, 50:181–187, August, 1965. In that article it was reported that researchers attempted to duplicate the reptilian anatomy to provide for better perfusion in human myocardium by perforating portions of the ventricular myocardium with 1.2 mm diameter needles in 20 locations per square centimeter. It has been shown that the perfusion channels formed by mechanical methods such as acupuncture generally close within two or three months due to fibrosis and scaring. Pifarre et al. evaluated the feasibility of direct myocardial revascularization from the left ventricle through artificially created channels. Their results are described in an article entitled "Myocardial Revascularization by Transmyocardial Acupuncture, A Physiologic Impossibility" in the Journal of Thoracic and Cardiovascular Surgery, 58:424–431, September, 1969. Pifarre et al. concluded that results were not encouraging. As a result, these types of mechanical approaches were abandoned in favor of other methods to effect the transmyocardial revascularization (TMR).

Similar revascularization techniques have involved the use of polyethylene tubes, endocardial incisions, and the creation of perforated or bored channels with various types of needles, and needle acupuncture. For example, T-shaped tubes have been implanted in the muscle, with the leg of the T-tube extending into the ventricular cavity as reported by Massimo et al. in an article entitled "Myocardial Revascularization by A New Method of Carrying Blood Directly From the Left Ventricular Cavity into the Coronary Circulation" appearing in J. Thorac. Surg., 34:257–264, August, 1957. In an article entitled "Experimental Method For Producing A Collateral Circulation To The Heart Directly From The Left Ventricle" by Goldman et al. in the Journal of Thoracic and Cardiovascular Surgery, 31:364–374, March 1965, several experimental methods for myocardial revascularization are described. One method involved the implantation of excised perforated carotid arteries into the left ventricular wall. Goldman et al. also examined the use of implanted perforated polyethylene tubing in a similar fashion.

U.S. Pat. No. 5,591,159 (Taheri) describes a device for effecting myocardial perfusion that utilizes slit needles to perforate the myocardium. The device uses a trans-femoral approach to position the device into the left ventricle of the patient. A plunger is activated to cause the needles to enter the myocardium several times. Perforation of the myocardium may be effected by means of a laser beam transmitted through the lumen of the needle or high velocity drill.

U.S. Pat. No. 5,655,548 (Nelson et al.) describes a method for perfusing the myocardium using a conduit disposed between the left ventricle and the coronary sinus. In one method, an opening is formed between the left ventricle and the coronary sinus, and the coronary ostium is partially occluded using a stent that prevents the pressure in the coronary sinus from exceeding a predetermined value. Blood ejected from the left ventricle enters the coronary sinus during cardiac systole. The apparatus limits the peak pressure in the coronary sinus to minimize edema of the venous system. The system utilizes retroperfusion via the coronary sinus of the venous system.

U.S. Pat. No. 5,755,682 (Knudson et al.) describes a device that establishes a channel leading directly from a chamber of a heart to a coronary artery. In one described method, a channel is created that extends through the deep coronary arterial wall through underlying cardiac musculature into the underlying chamber of the heart by using a scalpel, electro-surgical cutting blade, laser, or by radio-frequency ablation. A device is placed inside the channel to conduct blood from the heart chamber into the coronary artery.

Previous researchers had explored long term retroperfusion via the coronary sinus but found that its leads to edema of the cardiac veins which are incapable of sustaining long-term pressures above about 60 mm Hg. The procedure basically places a stent-like plug in the left ventricle so that blood flows into the coronary sinus and then into the myocardium via the venous system using retroperfusion, not into the myocardium directly. In the aforementioned Nelson et al. patent there is disclosed the use of a cutting instrument, such as a cannulated needle, a rotating blade, or medical laser to provide the required opening for the conduit. It is believed that when implanted in the heart, the plug and stent will result in long-term retrograde perfusion of the myocardium using the cardiac venous system and will cause a redistribution of the flow within the venous system so that a greater fraction of the deoxygenated blood will exit through the lymphatic stem and the Thebesian veins (any of the minute veins of the heart wall that drain directly into the cavity of the heart). The inventors also describe the use of a conduit that takes the place of the coronary sinus.

Researchers have also evaluated the used of lasers to create channels in the myocardium. U.S. Pat. No. 4,658,817 (Hardy) describes a surgical carbon dioxide laser with a hollow needle mounted on the forward end of the handpiece. The needle is used to perforate a portion of the tissue, for instance the epicardium, to provide the laser beam direct access to distal tissue of the endocardium for lasering and vaporization. The device does not vaporize the tissue of the outer wall instead it separates the tissue which recoils to its native position after the needle's removal. This technique eliminates surface bleeding and the need for suturing the epicardium as is done with other techniques. The device includes a port that allows the needle to be cleaned via an injection of saline.

In U.S. Pat. No. 5,607,421 (Jeevanandam) discloses that laser channels remain open because carbonization associated with the laser energy inhibits lymphocyte, macrophage, and fibroblast migration. Thus, in contrast to channels created by needle acupuncture, laser channels heal more slowly and with less scar formation, which allows endothelialization and long term patency.

An article entitled "New Concepts in Revascularization of Myocardium" (by Mirhoseini et al. in Ann. Thor. Surg., 45:415–420, April 1988) discusses the work of investigators exploring several different approaches for direct revascularization of ischemic myocardium. One revascularization technique utilizes "myoepexy", which consists of roughening of the myocardial surface to enhance capillarization. Another technique, known as "omentopexy" (the operation of suturing the omentum to another organ), consists of sewing the omentum over the heart to provide a new blood supply. Another approach involves implanting the left internal mammary artery directly into heart muscle so that blood flowing through the side branches of the artery will perfuse the muscle.

It has been reported by Moosdorf et al. in their article entitled "Transmyocardial Laser Revascularization—Morphologic Pathophysiologic And Historical Principles Of Indirect Revascularization Of The Heart Muscle" in Z Kardiol, 86(3): 147–164, March, 1997 that the transmyocardial laser revascularization results in a relevant reduction of clinical symptoms such as angina and an increase of exercise capacity in approximately two thirds of the patients treated. Objective data of enhanced myocardial perfusion as assessed by positron emission tomography, thallium scans, and stress echocardiography has also been presented in other studies. Some researchers have found that TMR channels created by CO2 lasers are surrounded by a zone of necrosis with an extent of about 500 microns. In heart patients who died in the early postoperative period (1 to 7 days) almost all channels were closed by fibrin clots, erythrocytes, and macrophages. At 150 days post procedure, they observed a string of cicatricial tissue (scar tissue resulting from the formation and contraction of fibrous tissue in a flesh wound) admixed with a polymorphous blood-filled capillary network and small veins, which very rarely had continuous links to the left ventricular cavity. At the 2-week post procedure point a granular tissue with high macrophage and monocyte activity was observable. See for example, the article by Krabatsch et al. entitled "Histological Findings After Transmyocardial Laser Revascularization" appearing in J. Card. Surg. 11:326–331, 1996, and the article by Gassler et al. entitled "Transmyocardial Laser Revascularization. Historical Features In Human Nonresponder Myocardium" appearing in Circulation, 95(2): 371–375, Jan. 21, 1997.

PLC MEDICAL's (Franklin, Mass.) Heart Laser and Eclipse's (Sunnyvale, Calif.) TMR 2000 laser revascularization system's have recently been clinically tested and neither device has shown significant survival benefit between laser-based transmyocardial revascularzation and medical management. However, in general the use of the devices did result in a two-class reduction in angina symptoms in the months following the procedure. Recent data was reported with respect to fuctional improvement, long-term survival, and angina relief after three years in 70 patients suffering from refractory angina yet not amenable to conventional revascularization. The patients were treated with PLC's CO2 Heart Laser. After the revascularization procedure with the Heart Laser, the angina class reduction seen at the first year persisted for at least three years with an accompanying increase in exercise tolerance. A significant increase in long-term mortality was not observed, however.

To date, studies have shown that no matter which laser, CO2 or Holmium are used, the clinical results following a laser-based transmyocardial revascularization procedure were almost identical: patients had an increase in exercise tolerance, a two-class reduction in angina symptoms, and no significant alteration in left ventricular ejection. BAXTER, J&J, CARDIODYNE and BARD/CORMEDICA are other companies that are also exploring laser-based TMR systems.

In co-pending U.S. patent application Ser. No. 08/958, 788, filed on Oct. 29, 1997, U.S. Pat. No. 5,980,548, entitled Transmyocardial Revascularization System, which is assigned to the same assignee as this invention and whose disclosure is incorporated by reference herein, there is disclosed a system making use of mechanically created punctures to provide the same benefits as laser-created channels by initiating a healing response and effecting denervation in the myocardium. In particular, that system makes use of implants within the myocardial tissue to perpetuate a foreign body or healing response. That application additionally discloses the use of pharmaceuticals, growth factors and genetic material to provide the heart with an initial and perpetuating stimulus for healing itself.

More recently, other researchers have had related ideas Pelletier et al. examined myocardial channels created by lasers and the resulting injury that leads to an angiogenic response mediated by a number of growth factors. This work is described by Pelletier in "Angiogenesis and Growth Factor Expression in a Model of Transmyocardial Revascularization" (Annals of Thoracic Surgery, 66:12–18, 1998). With similar thoughts in mind, other companies are also investigating non-laser alternatives for myocardial revascularization. ANGIOTRAX (Sunnyvale, Calif.) is investigating a percutaneous device and flexible tip surgical handpiece for mechanically creating channels. BOSTON SCIENTIFIC (Natick, Mass.) is working with ARTHROCARE on the development of a radio-frequency (RF) system for percutaneous TMR. The device creates holes in the myocardium with needle electrodes that deliver RF energy at 450 kHz. The device utilizes a catheter that has been designed by SciMed. RADIUS MEDICAL (Maynard, Mass.) is exploring a percutaneous RF devices that utilizes a hollow guidewire, 0.021 or 0.035 inches in diameter that utilizes 13 kHz, that is passed through a 6 French diagnostic catheter. Contrast media is injected through the hollow wire to help position the device tip against the endocardial tissue. RADIUS believes that the hollow wire can be used to infuse proteins or genetic material into the myocardium. U.S. Pat. No. 5,810,836 (Hussein et al.) describes a stent for insertion into a heart wall for transmyocardial revascularization. The device generates needle-made, or drilled, channels in the heart wall. A stent is implanted in each channel to maintain the patency of the channel. In European Patent Application No. 97107784.7, assigned to United States Surgical of Norwalk, Conn., a coring device is described for removing tissue during a biopsy or transmyocardial procedures. The coring member is rotatable and linearly advanceable at coordinated predetermined rates to core body tissue. The tissue can be cauterized during the coring procedure. European Patent Application number 98201480.5 and PCT International application number PCT/US98/08819 of C. R. BARD in Murray Hill, N.J. describes a "TMR stent and delivery system." That system includes a device which pierces the myocardial tissue and a stent which is implanted to permit the flow of blood from the left ventricle directly into the tissue for direct revascularization. Patent Cooperation Treaty (PCT) international application number PCT/US97/03523 of Energy Life Systems of Costa Mesa, Calif. describes a similar system. German patent number DE 296 19 029 U1 (Kletke) describes a needle for myocardial penetration. A needle is used to create a series of puncture canals. The canals are protected by the placement of continuous length of a resorbable suture, which is looped into each puncture.

In addition, researchers are exploring the percutaneous and direct surgical injection of growth factors and genetic material. Mack et al. describes experiments to improve myocardial perfusion in an article entitled "Biologic Bypass with the Use of Adenovirus-Medicated Gene Transfer of the Complementary Deoxyribonucleic Acid for Vascular Endothelial Growth Factor 121 Improves Myocardial Perfusion and Function in the Ischemic Porcine Heart" in The Journal of Thoracic and Cardiovascular Surgery 115:168–177, January 1998. Sanborn et al. described the potential injection of angiogenic proteins and genes directly into the heart via the endocardium with a percutaneous fluoroscopically guided system in an abstract entitled "Percutaneous Endocardial Gene Therapy: In Vivo Gene Transfer and Expression" in the Journal of the American College of Cardiology 33:262A, February 1999. Uchida et al. described growth factor injections in "Angiogenic Therapy of Acute Myocardial Infarction by Intrapericardial Injection of Basic Fibroblast Growth Factor and Heparin Sulfate: An Experimental Study" American Heart Journal 130:1182–1188, December 1995. Uchida utilized a catheter system for percutaneous transluminal administration of drugs through the right atrium into the pericardial cavity with a 23 gauge 4 mm long needle. U.S. Pat. No. 5,244,460 (Unger et al.) describes a method for inserting a catheter into a coronary artery and for infusing multiple coronary drug injections, containing blood vessel growth promoting peptides (i.e. fibroblast growth factor), through an infusion port into the catheter over a period of time.

In summary, there are a number of potential mechanisms which individually or in combination may be responsible for the improvements seen in patients subjected to the previously described myocardial revascularization techniques including: (1) new blood flow through the created channels, (2) angiogenesis (stimulation of the creation of new blood vessels), (3) cardiac denervation, (4) the placebo effect, (5) ablation of ischemic myocardium, and (6) formation of collateral circulation.

Currently it is believed that cardiac denervation and angiogenesis are the primary causes for post procedure angina relief and improved perfusion respectively. The injury damages nerves thereby minimizing the pain sensation and stimulates angiogenesis. While the aforementioned techniques and methods for revascularizing the myocardium offer some promise they never the less suffer from one disadvantage or another. As a first example, the lasers are very expensive to purchase. The aforementioned U.S. patent application, Ser. No. 08/958,788, filed on Oct. 29, 1997, U.S. Pat. No. 5,980,548 is directed to the same or similar medical benefits achieved by use of non-laser devices, such as those disclosed and claimed therein. As a second example, the design of the interventional cardiology catheter-based drug delivery systems appear unable to deliver drugs to tissues located beyond the arterial walls. Significant benefit could be gained by the delivery of agents (e.g. foreign body particles, drugs, growth factors, genetic material, etc.) into heart tissues beyond the arterial wall. Those devices that have considered direct injection of drugs or genetic material into the myocardium simply deposit the material within a channel that is typically created by a needle. As the myocardium dynamically contracts, deposits of materials in these channels will likely migrate unless stabilized with a mechanical or chemical anchor of some sort. It is the intent of this invention to overcome these and other shortcomings of the prior art.

OBJECTS OF THE INVENTION

Accordingly, it is a general object of this invention to provide a system and methods for treating targeted internal tissue, e.g., cardiac tissue or other internal tissue, of a living being which overcomes the shortcomings of the prior art.

It is a further object of this invention to provide a system and method for myocardial revascularization that overcomes the disadvantages of the prior art.

It is a further object of this invention to provide a system and method for vascularizing the cardiac tissue of a living being to cause the formation of lumens in communication with the being's arterial system.

It is a further object of this invention to provide a system and method for treating cardiac tissue of a living being to affect the conduction of electrical signals in the cardiac tissue.

It is a further object of this invention to provide a system and method for treating cardiac tissue of a living being to affect the conduction of nerve signals in the cardiac tissue.

It is a further object of this invention to provide a system and methods for treating targeted internal tissue, e.g., cardiac tissue or other internal tissue, by delivering flowable agent(s) thereto.

It is a further object of this invention to provide a system and methodology for providing relief from myocardial ischemia.

It is a further object of the present invention to provide a system having delivery capabilities delivering agents flowable agents to internal body tissues for beneficial purposes, such as, but not limited to treating heart disease.

It is a further object of this invention to provide apparatus and methods for providing myocardial perfusion that reduce the level of ischemia in a living being.

It is a further object of this invention to provide methods and apparatus for reducing the level of discomfort associated with angina in a living being.

It is a further object of this invention to provide apparatus and methods to enable living beings that suffer from the later stages of ischemic heart disease to experience reduced pain and improved emotional well being.

It is a further object of this invention to provide a transmyocardial revascularization system and methodology that is simple and cost effective.

It is a further object of this invention to provide an apparatus and method for myocardial revascularization to increase blood flow to the myocardium from the endocardium without using the native diseased coronary arteries.

It is a further object of this invention to provide an apparatus and method for myocardial revascularization to be used with living beings having extensive coronary atherosclerosis.

It is a further object of this invention is to provide apparatus and methods for effecting endovascular myocardial revascularization.

It is a further object of the present invention to provide methods and apparatus which can be utilized either in open surgical, minimally invasive surgical, or transluminal techniques to deliver beneficial agents to the myocardium.

It is a further object of this invention to provide a system and method for direct myocardial revascularization without the need for opening the chest cavity.

It is a further object of this invention to provide as system and method for direct endovascular myocardial revascularization without having to utilize a laser, although a laser may be used, if desired, in some applications as part of the procedure.

It is a further object of this invention to provide a system and method to create channels in the myocardium without having to utilize a laser, although a laser may be used, if desired, in some applications as part of the procedure.

It is a further object of this invention to provide a system and method for effecting initial and prolonged stimulus within the myocardium that instigates the heart to heal itself.

It is a further object of this invention to provide instruments with delivery capabilities for dispersing flowable agent(s) into targeted internal tissues of a living being at a location beyond that which is immediately adjacent the instrument.

SUMMARY OF THE INVENTION

These and other objects of this invention are achieved by providing tissue, e.g., cardiac, treatment systems and methods of treating tissue, such as the myocardium and other tissues, within the body of a living being.

The treatment system can be used for vascularizing the cardiac tissue of a living being to cause the formation of lumens in communication with the being's arterial system, or can be used to affect the conduction of electrical signals in the cardiac tissue, or can be used to affect the conduction of nerve signals in the cardiac tissue, or in some way beneficially treat other (e.g., non-cardiac) tissue within the body of the being.

To that end the treatment system comprises a delivery instrument and a flowable agent. The flowable agent comprises a plurality of small particles for introduction into the cardiac tissue or other tissue. The delivery instrument is arranged to introduce the flowable agent at or adjacent the cardiac or other targeted tissue by imparting a force to the agent, whereupon the agent directly enters the cardiac or other targeted tissue at an entry situs.

DESCRIPTION OF THE DRAWINGS

Other objects and many attendant features of this invention will become readily appreciated as the same becomes better understood by reference to the following detailed description when considered in connection with the accompanying drawing wherein:

FIG. 14 is a side sectional view of an embodiment of a delivery instrument, e.g., a flexible pressurized intravascular access delivery instrument, forming a portion of the tissue treatment system of the subject invention being used delivery agents through the urethra wall into the prostrate gland of a living being.

FIGS. 15A–15I are embodiments various exemplary types of particulate materials which may make up all or a portion of the flowable agent(s) of the subject invention, in this case the materials being in the form of microspheres and/or microparticles or other small particulates;

DETAILED DESCRIPTION OF THE PREFERRED EMBODIMENTS

Figure 1A:
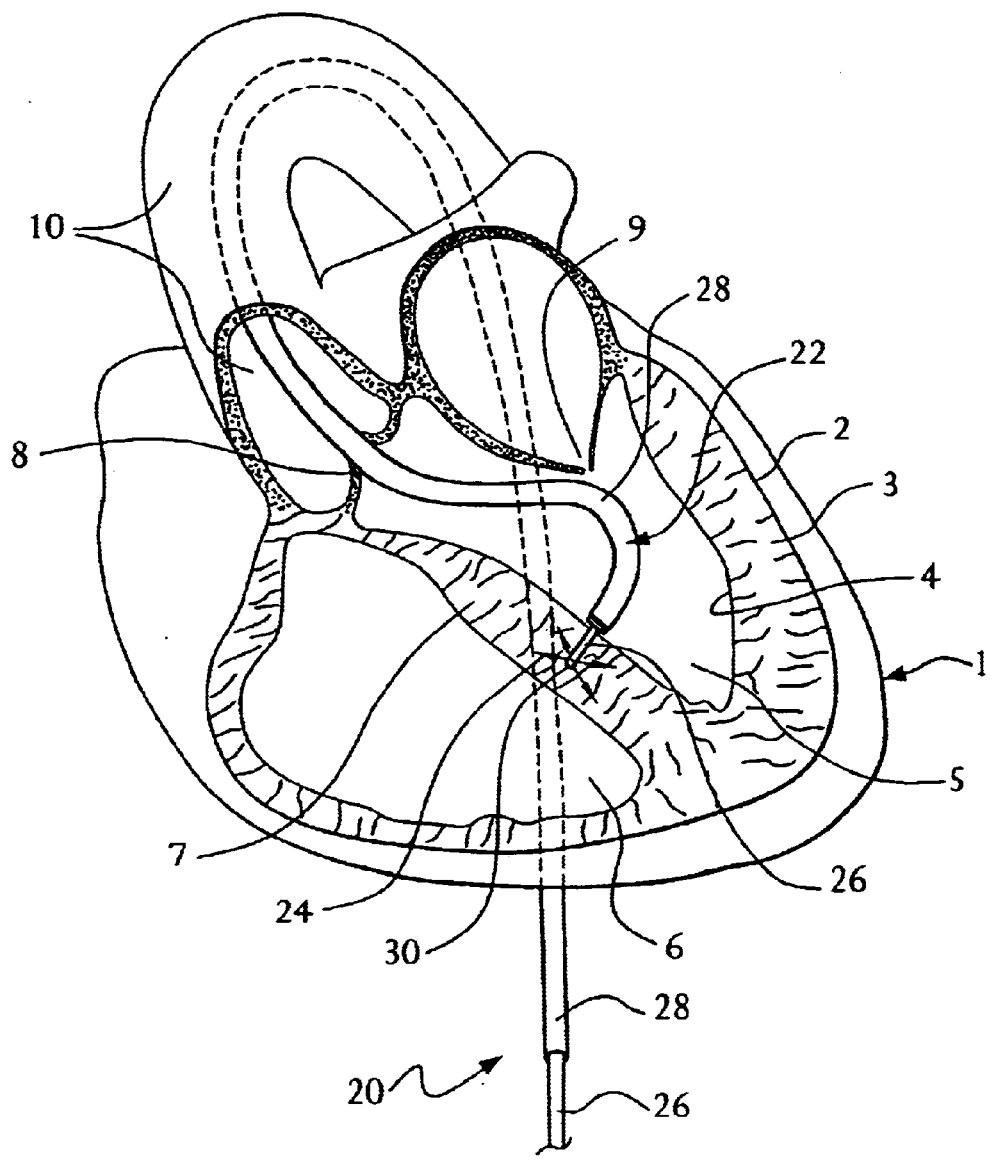
FIG. 1A is an illustration of the heart of a living human being, partially in section, showing one embodiment of a delivery instrument forming a portion of the tissue treatment, e.g., myocardial revascularization, system of the subject invention being used to penetrate a portion of the septum to deliver flowable agent(s) to the targeted tissue, e.g., the septum, via the endocardium.

Referring now to the drawing wherein like reference characters refer to like parts, there is shown in FIG. 1A the distal portion of a delivery subsystem 22 which will be described later and which forms a portion of a tissue treatment, e.g., revascularization system, 20 constructed in accordance with this invention.

These and other objects of this invention are achieved by providing tissue, e.g., cardiac tissue, treatment systems and methods of treating tissue, such as the myocardium and other tissues within the body. The systems basically comprise a delivery system for accessing a targeted tissue within the living being and a flowable agent (to be described in considerable detail later) arranged to be introduced into the targeted tissue by the delivery system.

In several preferred embodiments shown and described herein the tissue treatment system introduces the flowable agent into select portions of the myocardium, or other cardiac tissue.

As will be described later one or more of the delivery systems of this invention can be utilized during transluminal, transthoracic and direct surgical access procedures. Where appropriate, for example in the case of intraventricular access, portions of the delivery system are steerable to properly orient the delivery instrument. In some embodiments the delivery instruments are arranged to pierce the heart tissue and create channels extending from the endocardium, the epicardium, or the cardiac vessels. When tissue penetration is utilized, the delivery instrument can include a feature to control the depth of penetration. To minimize bleeding through the channels the delivery instrument can dilate small initial punctures that later contract down after device removal. When the formation of channels is required, this can be achieved, by way of example, with a rotary-tipped device, pressurized fluid jet devices, vibratory instruments and piercing needle-like tip devices.

The tissue treatment systems of this invention may utilize some form of mechanical action or application of energy, e.g., electrical, sonic, thermal, optical (e.g., laser), pressurized fluid, radio frequency (RF), nuclear, in the process. The mechanical action or energy application may affect the surroundings tissues at a distance from the delivery system. For example, thermal energy may be conducted away via nerve conduits thereby disabling the nerves and creating a condition of denervation. As another example, shockwaves created by sonic energy may travel through the tissue and serve to initiate a change that is beneficial to the patient either immediately or over time.

The delivery instruments may make use of a device to stabilize a portion of the system or anatomy during the procedure (e.g., a vacuum stabilizer or surgical stabilizer ring). A controller may also be provided as part of the system to coordinate the operation of the delivery instrument with the cardiac cycle. For example, power to the delivery instrument can be synchronized with EKG leads, such that delivery instrument operation occurs at a recurring portion of the cardiac cycle.

Radiopaque contrast media, fluoroscopy, ultrasound, magnetic resonance, GPS-like triangulation, RF triangulation, flashback or other imaging/position systems can be used to orient/position the delivery instrument during the procedure. Robotics could also be used to position the delivery instrument of the system in a body cavity or lumen. For example, a robotic arm can be used to navigate within the chest cavity through a small thoracic incision to position the delivery instrument in relation to the epicardium.

In some applications, the delivery instrument is arranged to directly deliver the flowable agent(s) into the cardiac tissue. In other applications a pressurized system imparts kinetic energy to the flowable agent(s) for the purpose of dispersing the agents into the tissue located beyond the tissue immediately adjacent the delivery instrument of the system. Control parameters on the delivery instrument (e.g. a pressure limiter) can provide control over agent penetration depth.

In some applications the dispersal pattern for the flowable agent(s) can be selected and adjusted to provide for an optimum dispersion of the agent into the targeted tissue.

In applications, the pressurized system of the delivery instrument delivers the agents from the coronary vessels, the endocardium or the epicardium into the myocardium without the need to pierce the tissues of the artery, endocardium or epicardium. The delivery instrument can use a gas, fluid, gel, or other suitable carrier to transport the flowable agent through the instrument and into contact with the tissue.

Although the preferred embodiment of the system will allow delivery of the agents into distant tissues, it may be beneficial to deposit some of the agents within an instrument created channel or to deliver a portion of the agent systemically via the circulatory system. Agents can pre-dosed in per-use packages or the system can draw doses of pre-selected volumes from a reservoir. The system can vary the concentration of the agent in a fluid, or other suitable carrier.

In accordance with some preferred embodiments of this invention the flowable agents are formed of at least one material that can elicit a beneficial response within the tissues. For example, at least a portion of the agents can be comprised of such items as a pharmaceutical, a growth factor, a suitable biomaterial, or a genetic or cellular based material. The presence of the agent can initiate a biochemical/biological process that stimulates the tissue to heal itself. The agents can also trigger the onset of a foreign body or healing response to cause the formation of lumens in communication with the arterial system.

The flowable agents can be designed to assist the tissue in functioning more effectively. For example, the agents could contain an electrically conductive element that modifies or improves the contractile motion of the myocardium. It is contemplated that the mere presence of even an inert agent in the tissue may also be beneficial to a living being. Thus, for example, one embodiment of the invention described herein can be used to deliver a select agent from within the urethra through the urethra wall and into the sphincter muscle to bulk up the sphincter as a remedy for urinary incontinence. As another example the system could be used to overcome the difficulty of transporting pharmaceuticals across the blood-brain by providing positioning a portion of the system in the vicinity of the targeted tissue (e.g., brain tumor) and delivering beneficial agents. As yet another example, the system of the subject invention could be used to disperse beneficial agents (e.g. gene-based elements) into the musculature of a patients with degenerative muscle diseases (e.g., muscular dystrophy).

The flowable agents may be totally resorbable, partially resorbable or non-resorbable. As an example they can be made of polymers, metals, elastomers, glass, ceramics, collagen, proteins or other suitable materials or a combination materials. A collection of agents with varying characteristics (e.g. density) can be delivered to the tissue to allow for a graduated deposition of varying types of agents to different depths of the tissue. Other agent characteristics (e.g. texture and abrasiveness) can be controlled to allow for varying degrees of trauma to encountered tissues. Where the agents incorporate a solid component, the shape of the component can be varied from spheres to fibers to any other desired shape. A form of a microsphere may be utilized to treat the desired tissue region either by occupying space or by stimulating a biological response to the presence of them material or the release from the material of some chemical or biological element.

In the treatment of cardiac tissue, the presence of the flowable agents of this invention when deployed in the myocardium will not appreciably restrict the cardiac contraction of the heart.

The flowable agents may be constructed to effect a time-phased delivery of active ingredients. In summary, both the creation of channels and the dispersion of the agents is designed lead to improvements in patients with cardiovascular disease as a result of: (1) angiogenesis (stimulation of the creation of new blood vessels), (2) cardiac denervation (3) ablation of ischemic myocardium, and (4) formation of collateral circulation.

Turning now to FIG. 1A, there is shown a portion of a cardiac vascularization system 20 in the process of revascularizing the myocardium of a living, e.g., human, being. The entire system 20 is shown in detail in FIG. 5A and will be described in detail later. Suffice it for now to state that the treatment system 20 includes various components and subsystems which cooperate to effect the delivery of flowable agents into relevant tissue of the being, e.g., the heart, the vascular system, etc. FIG. 1A is an illustration, not to scale, of a section of a healthy, human heart 1. As can be seen, the heart includes the epicardium 2, the myocardium 3, the endocardium 4, the left ventricle 5, the right ventricle 6, the ventricle septum 7 the aortic valve 8, the mitral valve 9, and the aorta 10. As can be seen clearly in FIG. 1A, the distal portion of the delivery subsystem 22 of system 20 is shown penetrating the ventricle septum and delivering the flowable agent(s) 24, which are denoted by the arrows in that illustration, into the adjacent tissues of the septum. The subsystem 22 includes a delivery instrument 26 and a conventional, e.g., Judkins, guiding catheter or instrument 28. The delivery instrument 26 of this embodiment basically comprises an elongated catheter having a high-speed, rotary working head 30 located at the distal end thereof. The guiding instrument 28, which will be described later, is positioned to guide the delivery instrument 26 to the desired location at the ventricle septum. The high speed working head 30 of the delivery instrument is arranged to propel and disperse the flowable agent into the adjacent tissue. The flowable agent may be any type of flowable material, e.g., a fluid that alone or in combination with other additives such as drugs, growth factors, biocompatible microparticles, etc., is to be introduced into the relevant tissue for a desired purpose. The details of various of the flowable agents will be described later. When the delivery instrument 26 is operated, its working head, e.g., the rotary working head of the embodiment described heretofore, or other types of working heads, ejects or bombards the surrounding tissue with the propelled flowable agent(s) 24 at high pressure to force the agent(s) into the tissue by increasing the local dynamic or hydrostatic pressure induced by the agent or the rotating working head. The construction of the delivery instrument 26 allows the agent(s) 24 to be delivered and dispersed into a significant volume of cardiac tissue.

It is important to note at this juncture that most prior art systems for delivering medications to the heart do so either systemically by vein or regionally, e.g., intracoronary infusion. Systemic delivery is not efficient for the treatment of locally isolated disease for various reasons, namely: a wide range and large number of sites are exposed to the material, large quantities of the agent are required, due to the entire volume of distribution, to obtain the desired effect, and the agent degrades and can be eliminated by various organ systems that keep the agent from reaching the target site, thereby reducing the agent residence time in the body.

As utilized in this invention, local intra-tissue delivery of the flowable agent(s) 24 eliminates these problems. In particular, the flowable agent(s) is (are) distributed into the target tissue and not just deposited into the channel or puncture created in the tissue. The nature of the pressurized flowable agent carries it to intra-cellular sites beyond the site of the initial puncture.

As will be appreciated by those skilled in the art, penetration into the target tissue is a function of the mass, density and speed of the agent(s). The agent(s) is (are) less likely to migrate away from the site of implantation. When the treatment of the site is complete, the delivery instrument 24 can be repositioned and the procedure repeated to impregnate a new treatment site with the selected agent(s).

It is believed that the systems of the subject invention may be used as sole therapy for end-stage heart disease patients that are not amenable to alternative therapies, such as coronary artery bypass surgery, or the systems could be used as an adjunctive therapy in addition to other cardiac therapies such as PTCA, stenting, or coronary artery bypass surgery.

Figure 1B:
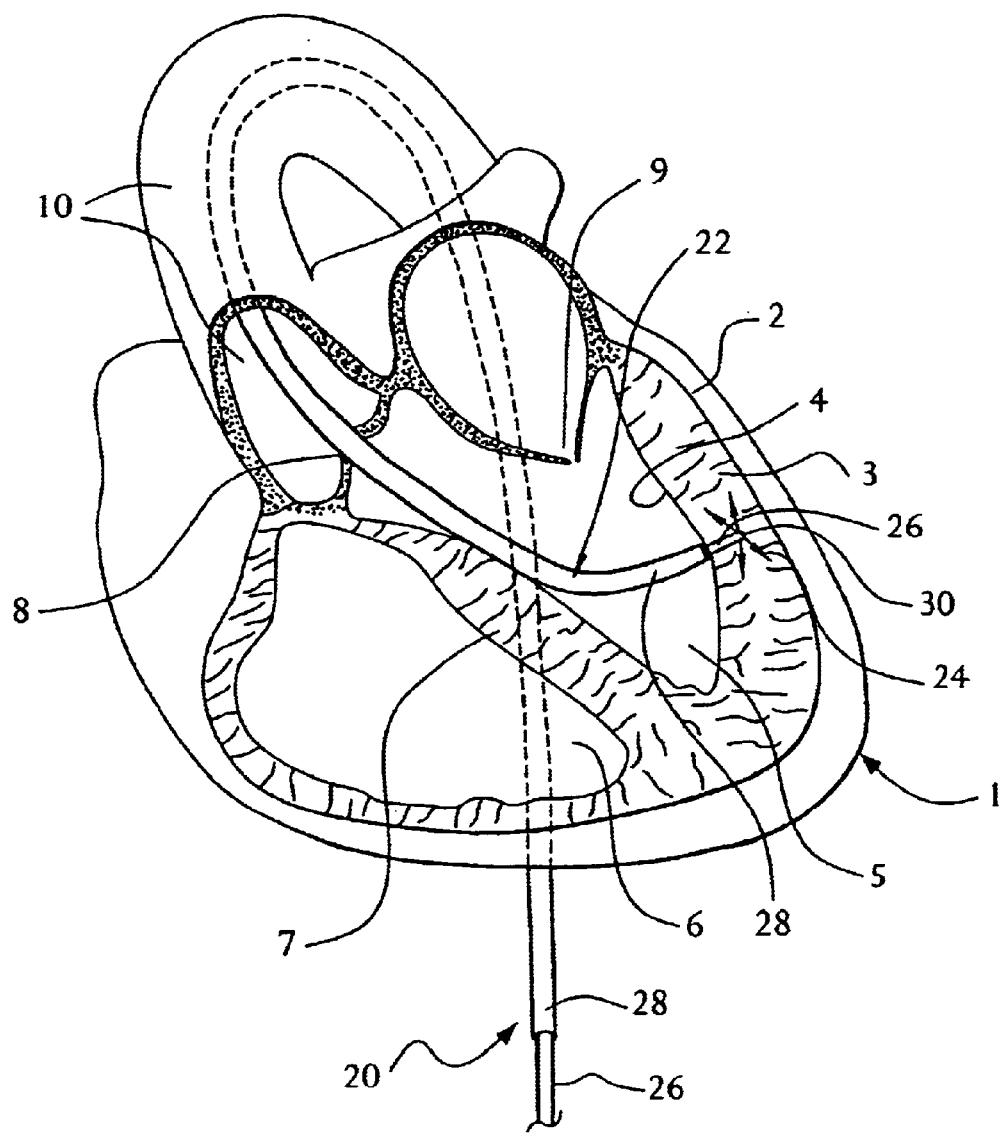
FIG. 1B is an illustration similar to that of FIG. 1A, but showing the embodiment of the delivery instrument being used to penetrate a portion of the myocardium to deliver the flowable agent(s) into the myocardium via the endocardium.

FIG. 1B illustrates a portion of a transmyocardial revascularization system 20 like that shown in FIG. 1A and constructed in accordance with this invention and shown in the process of revascularizing the myocardium 3. In this illustration, the guiding instrument 28 is positioned to guide the delivery instrument 26 toward the desired location on the myocardium adjacent the left ventricle. The distal portion of the delivery instrument 26 is shown penetrating the myocardium and delivering the agent(s) 24, which are also denoted by the arrows, into the adjacent tissue of the myocardium.

Figure 2:
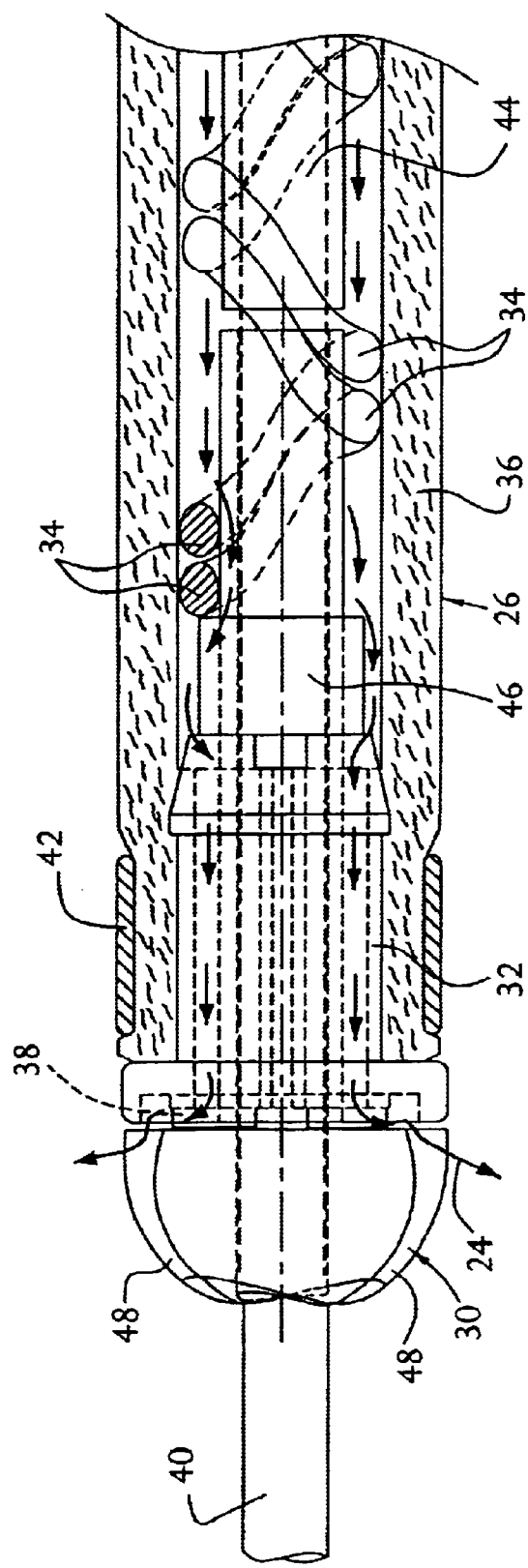
FIG. 2 is an enlarged sectional view of the distal portion of the delivery instrument embodiment illustrated in FIGS. 1A and 1B, and showing the flow paths of the agent(s) through and out of the instrument for dispersion into the targeted tissue.

FIG. 2 is an enlarged sectional view of the distal end portion of the delivery instrument 26 which is illustrated in FIGS. 1A and 1B, and showing the tissue penetrating system, utilizing the flow path of the agent(s) 24 through and out of the instrument. In accordance with one preferred embodiment of this invention, the instrument is constructed in a fashion similar to those described in U.S. Pat. No. 4,747,821 which is assigned to the same assignee as this invention and whose disclosure is incorporated by reference herein. To that end, the working head 30 is a rotary member which is arranged to revolve at a high speed in a bush 32 driven by a double helical drive wire 34 from a remote, proximally-located motor or turbine (not shown). The bush 32 is mounted on the distal end of a flexible or rigid catheter jacket 36. The agent(s) 24, under distribution, is delivered to the proximal end of the delivery instrument 26 (not shown) and is transported down a central passageway therethrough alongside and between the helical drive wires 36 to the bush 34, where the agent(s) 24 passes out of plural grooves 38 provided in the center and end of the front portion of the bush, whereupon the agent(s) is further energized as it is centrifuged by the rotation of the working head. The working head is arranged to revolve over a conventional guide wire 40, if one is needed for the procedure. The bush 34 is held in place at the distal end of the jacket by a retention band 42. A liner sleeve 44 extends down the center of the double helical drive wires 36. The distal end of the drive wires are fixedly secured, e.g., welded to a central shaft 46 of the working head 30. The distal end of the working head is a generally dome-shaped cam member having flatted or relieved surfaces 48.

Figure 4A:
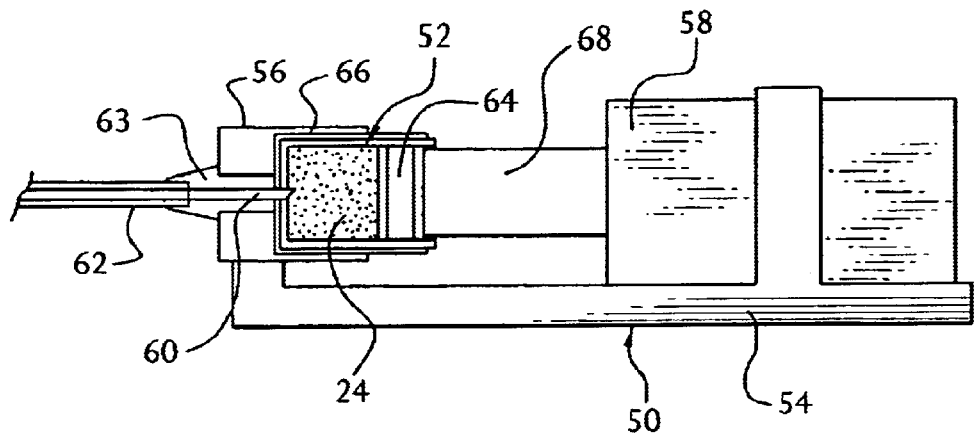
FIG. 4A is an enlarged side elevational view, partially in section, of the embodiment of the needle access capsule of FIG. 3B, positioned within a capsule injector forming a portion of the delivery instrument of FIG. 1.
Figure 4B:
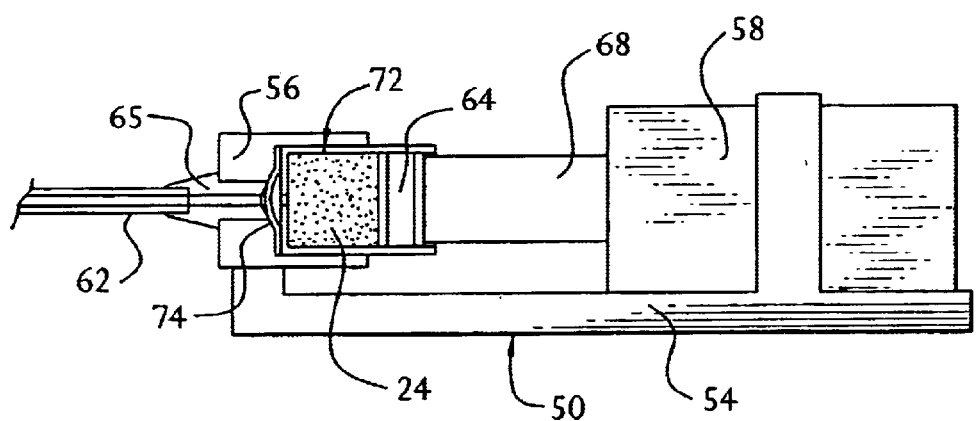
FIG. 4B is an enlarged side elevational view, partially in section, of the embodiment of the rupturable capsule of FIG. 3A, positioned within a capsule injector forming a portion of the delivery system of FIG. 1.

FIGS. 4A and 4B show two examples of delivery injectors forming a portion of the system 20 for propelling the flowable agent(s) 24 into any of the delivery instruments of this system, such as the delivery instrument 26 described heretofore. In particular, FIG. 4A shows a device 50 for propelling the agent(s) 24 from a rupturable, capsule 52. The injector 50 basically comprises a base plate 54 on which are mounted a capsule receiver 56 and a jack assembly 58. A needle 60 and associated tubing 62 forming a subassembly are mounted in the receiver 56. The tubing 62 is connected to a "highest wins valve" (to be described later) forming a portion of the system 20 for providing the flowable agent(s) to the delivery instrument 26 at the proximal end thereof. Another tube or conduit (also to be described later) is in fluid communication with the highest wins valve and the interior of the delivery instrument 26 so that the flowable agent(s) which will be provided through the tubing 62 enters into the instrument 26 flows therealong, as described above, and exits out of the instrument at the working head.

Figure 3A:
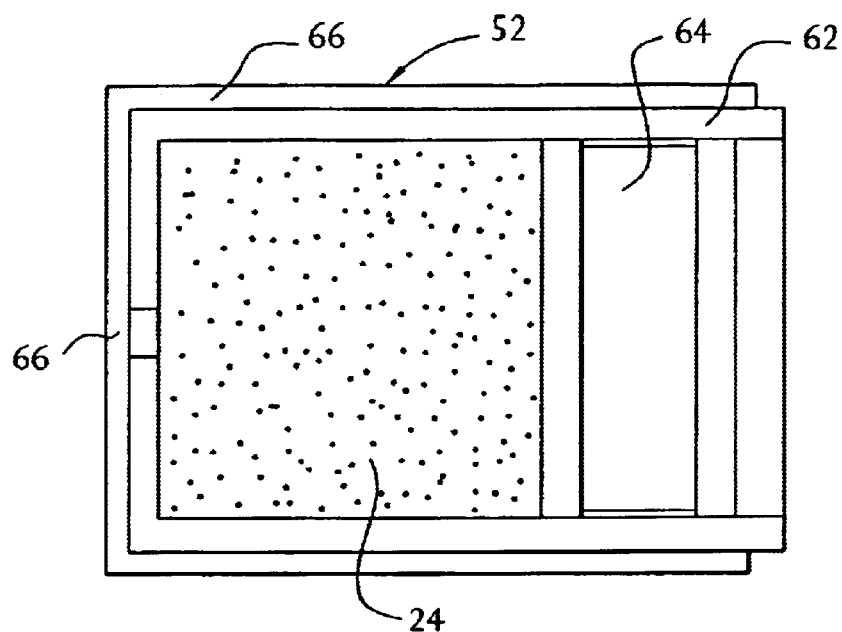
FIG. 3A is an enlarged side sectional view of one embodiment of a rupturable capsule containing a dose of the flowable agent(s) for delivery into the targeted tissue by various delivery instruments of the subject invention.

An enlarged view of the capsule 52 is shown in FIG. 3A. Thus, as can be seen therein, the capsule 52 comprises a container 62, made of a plastic such as polypropylene, and has a piston 64 at its proximal end. The piston 64 is made from a rubber compound similar to that used in medical syringes, and fits firmly, but slidably, in the container 64. On the distal end of the container 64 is a rubber coating 66 which seals the agent(s) 24 within the capsule 52. The coating may also be located along the walls of the container 62, such as shown in FIG. 3A.

Referring again to FIG. 4A, it can be seen that in use the capsule 52 is placed into a recess within the receiver 56 of the delivery injector and the piston 64 is driven toward the distal end of the capsule by a ram 68 of the jack assembly 58. This causes a sharp piercing end portion of the needle 60 in the delivery device 26 to pierce the rubber 66 whereupon the flowable agent(s) 24 flows into the delivery device 26 via the tubing 62 at a pressure determined by the rate of travel of the ram 68 and the impedance of the distal located passageways, e.g., the tubing 62, the passageway through the instrument 26, and the outlet delivery ports (e.g., the grooves 38 at the working head 30 see FIG. 2).

FIG. 4B shows a similar injector device 70 for propelling the agent(s) 24 from the capsule 72. The injector 70 is virtually the same as the injector 50, except that it doesn't include a needle 60. Thus, as can be seen, the injector 70 basically comprises a base plate 54 on which are mounted the capsule receiver 56 and the jack assembly 58. A tubing assembly 56 including tubing 62 is mounted on the receiver 56.

Figure 3B:
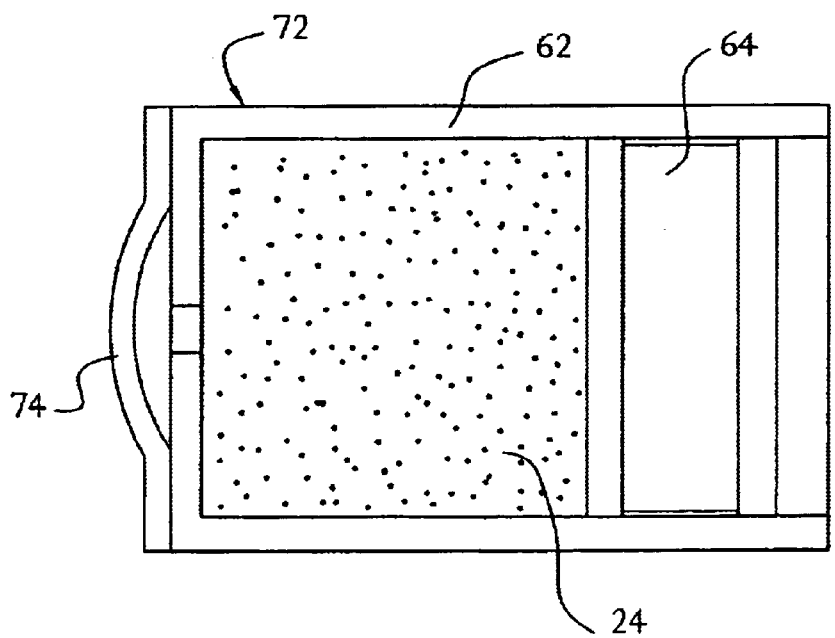
FIG. 3B is an enlarged side sectional view of one embodiment of a piercable capsule containing a dose of the flowable agent(s) for delivery into the targeted tissue by various delivery instruments of the subject invention.

An enlarged view of the capsule 72 is shown in FIG. 3B. Thus, as can be seen, that capsule comprises a container 62, made of plastic such as polypropylene, having a piston 64 at its proximal end. The piston is made from a rubber compound similar to that used in medical syringes and fits firmly, but slidably, in the container 62. On the distal end of the container is bonded a thin, frangible disk 74. The disk 74 is formed of aluminum foil or a similar material and is coated with a plastic, such as polyethylene, on its agent-contacting side (the inside). The disk serves to seal the agent(s) 24 within the capsule 62. The coating on the disk also acts as a hot-seal medium when bonding the disk to the container.

Referring again to FIG. 4B, in use the capsule 72 is placed into a recess within the receiver 56 and the piston 64 is driven toward the distal end of the capsule 72 by the ram 64 of the jack assembly 58. As the pressure of the agent(s) 24 rises, the disk 74 ruptures and the agent flows through the associated port into the tubing 62 and the associated instrument 26 at a pressure determined by the rate of travel of the ram and the impedance of the distal tubing and delivery ports, like that described earlier.

Figure 5A:
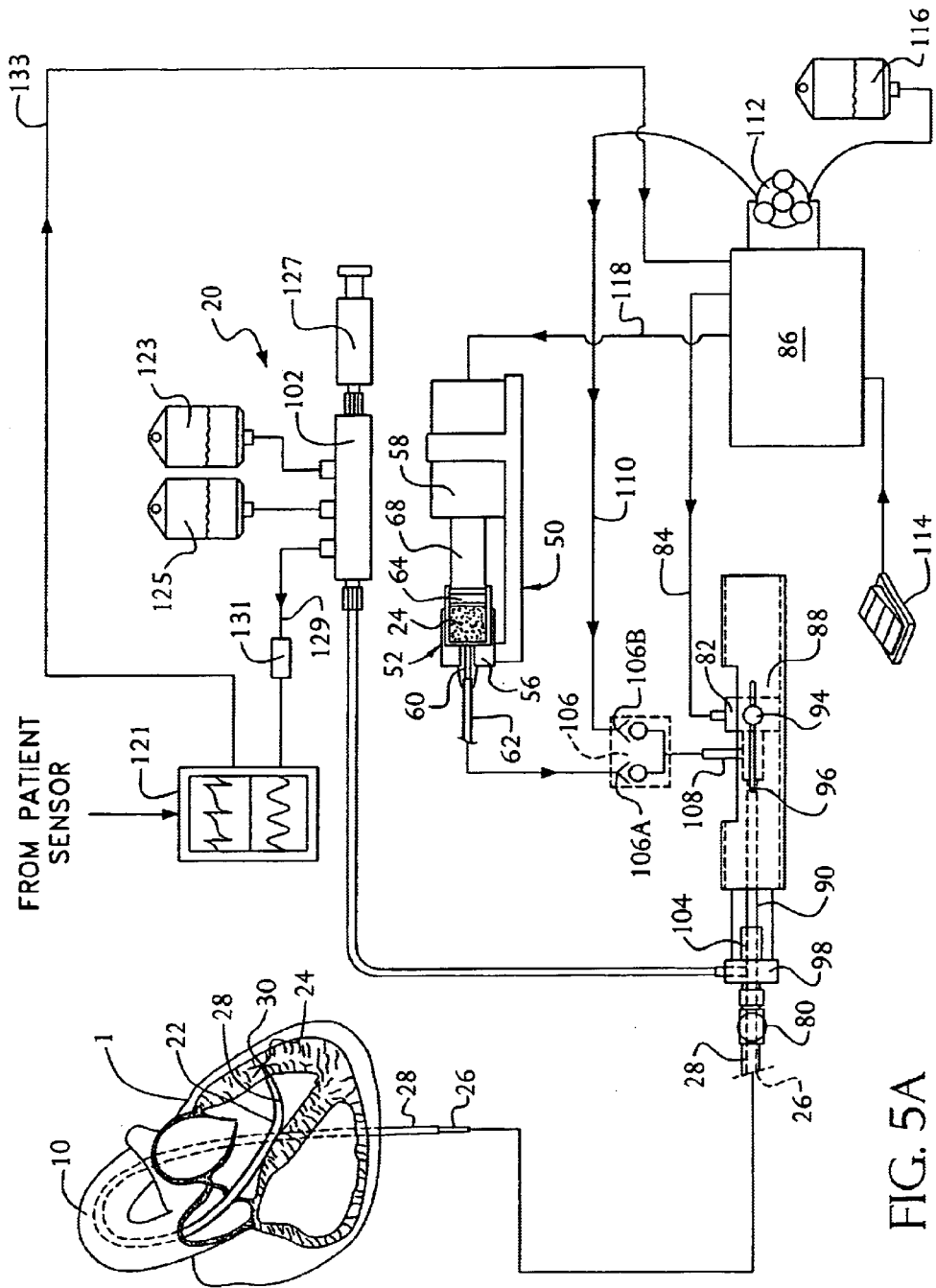
FIG. 5A is a schematic diagram and system illustration showing one embodiment of an entire targeted tissue treatment system making use of the delivery instrument of FIG. 1 for delivering the flowable agent(s) into a portion of the myocardium in accordance with the vascularization technique illustrated in FIG. 1B.

FIG. 5A is a schematic diagram and system illustration showing one embodiment of the entire system 20. That system includes not only the guide instrument 28 and the delivery instrument 26 but also means to control the operation of the delivery instrument in accordance with the subject invention. The illustration of FIG. 1B shows only a portion of the system 20 used to penetrate and deliver agent(s) 24 to a portion of the myocardium via the endocardium, whereas the illustration of FIG. 5A shows the entire system for achieving that end.

As mentioned, the delivery instrument 26 is a rotary device, whose distal end is shown in detail in FIG. 2. The device 26 is arranged to pass through the conventional guide catheter 28, which in this application is preferably a steerable, guide catheter. That catheter has a "J" shaped distal end and a knob 80 at the proximal end which used to steer the "J" shaped distal end as shown in FIG. 5A. The details of the steering mechanism are not shown in the drawing nor will be described hereinafter, but may comprise any suitable means for achieving such steering action, such as that disclosed in U.S. Pat. No. 5,674,197 (van Muniden et.al.), whose disclosure is incorporated by reference herein. The "J" shape of the distal end of the guide catheter 28 permits the user to advance the delivery instrument 26 to the desired position against the endocardium and by rotation of the guide catheter about its longitudinal axis via the knob 80, the "J" shaped distal end can be directed to any area of the ventricle 5.

The rotary working head 30 of the instrument 26 is driven by the drive cable from a turbine 82, via compressed nitrogen provided through a line 84. The line 84 is coupled to a controller 86, whose construction and operation will be described later, which receives compressed nitrogen from a tank or other source (not shown). The turbine 82 is mounted in a cradle 88. The turbine 82 includes an output shaft which is connected via any suitable means (not shown) to the proximal end of the drive helices 34. The turbine 82 is connected to the proximal end portion 90 of the jacket 36 of the instrument 26 so that longitudinal movement of the turbine causes concomitant movement of the instrument 26. To that end, the turbine 82 is slidably mounted in the cradle 88 in a manner which permits the user to feed the delivery instrument 26 down the guide catheter 28 to the precise location by moving a knob 94 connected to the turbine to and fro in a longitudinally extending slot 96 in the cradle 88.

The steerable guide catheter 28 is coupled at its proximal end to a distal manifold 98, which in turn is connected via line 100 to a conventional angiographic manifold 102. The distal end portion of the instrument 26 extends through a conventional hemostasis valve 104 to prevent the egress of blood from the interior of the guide catheter.

The angiographic manifold 102 is a conventional device such as that commonly used in laboratories and thus will not be described in detail. It will suffice to say that the physician uses the manifold 102 to pass a contrast medium via the guide catheter 28 to the site of the delivery instrument's distal or working head 30 in the ventricle for assessment of the location of the guide catheter and the delivery instrument by fluoroscopy.

The flowable agent(s) 24 to be delivered by the delivery instrument 26 is provided in the capsule 62. The capsule is in turn mounted in the injector 50. The agent delivery tube 62 is connected to one input 106A of a conventional "highest wins" valve 106. The outlet from the valve 106 is connected via a line 108 into a port in communication with the interior passageway extending longitudinally through the jacket of the delivery instrument 26. The other input 106B to the valve 106 is provided via a line 110 from a peristaltic pump 112.

The controller 86 is an electrically powered device which is arranged to accept inputs from a two-position foot control switch 114 to drive the peristaltic pump. The peristaltic pump is connected via a line to a bag or supply of saline 116. The electrically powered controller 86 is arranged to provide power via line 118 to the ram 58 of the injector 50. In addition, as noted earlier, the controller 86 provides the compressed nitrogen via line 84 to the turbine 82 of the delivery instrument.

In use, the guide catheter 28 is extended from the patient entry situs, e.g., the femoral artery, through the vascular system under fluoroscope vision until its distal end is in the appropriate location within the ventricle. The delivery instrument 26 is then advanced through the guide catheter until its working head 30 at its distal end is adjacent the ventricular wall. The foot control switch 114 is then depressed by the operator to a first switch position to cause the turbine 82 of the delivery instrument to operate, whereupon saline from the bag 116 is delivered to the instrument. In particular, the saline is pumped by pump 112 into communicating line 110, through the input line 106B of the highest wins valve 106 and its communicating outlet line 108 into the interior passageway of the delivery instrument. From there it flows longitudinally down the central passageway whereupon it exits from the distal end or at the working head. The operation of the turbine effects the concomitant high speed rotation of the working head. The operator then grasps the slide knob 94 on the cradle 88 and pushes it forward while the working head is rotated at the high speed to advance the working head into the myocardium. The cam surfaces on the working head engage the myocardium tissue to form a bore or channel therein. Preferably, the channel is made approximately one centimeter deep by the advancement of the instrument with respect to the catheter. This action is accomplished rather quickly, e.g., in about five seconds. Once the channel or bore is completed, or during the time of its formation, the foot control switch 114 is depressed by the operator further to the second switch position. This action results in electric power being provided via the controller 86 to the injector 50. In particular, electrical power is provided via line 118 to the jack of the controller, whereupon the jack commences inward movement, thereby causing immediate delivery of the agent (s) 24 into the tubing (the pushing of the ram causes the capsule to be pierced by the piercing needle 60 whereupon the agent flows through the needle into the communicating tubing 62, through the inlet port 106A of the highest wins valve (since this is port will now be at a higher pressure level than port 106B), whereupon the flowable agent will flow through communicating outlet line 108 into the interior of the delivery instrument 26 at the proximal end thereof. The agent is delivered down the delivery instrument to the working head either by continued motion of the ejector (assuming the capsule charge is large enough) or is carried forward by the continuing flow of saline from the pump 112. It is expected that the delivery of the agent(s) 24 from the capsule to the bore within the myocardium be delivered quite quickly, e.g., in five seconds or less.

In accordance with one preferred use of the system of the subject invention, e.g., the vascularization of the myocardium, plural bores, lumens or channels are formed in the myocardium by repeating the procedure as set forth above. As should be appreciated by those skilled in the art, the number of bores or channels, their size (e.g., inner diameter and depth), their spacing, and the tissue area encompassed thereby will be a matter of choice based on the desires of the operator of the system and the particular tissue treatment desired. For myocardial vascularization applications of this invention it is contemplated that the bores or channels created be within the range of ¼ to 3 mm in diameter, extending in depth from 1–20 mm, and being spaced from one another by 0.25 cm to 5 cm. The area coverage of cardiac tissue encompassed by the bores or channels may be from 1 to 100 square centimeters. Moreover, the size of the particles forming the flowable agent(s) or included in the flowable agent(s) will, of course, be a factor in the determination of the dimensions, spacing and geographic extent of the channels in the targeted tissue.

If it is desired to time the introduction of the delivery system and the flowable agent(s) 24 into the myocardium to any particular portion of the patient's cardiac cycle (e.g., during diastole) then the system 20 preferably includes a cardiac cycle monitor 121 for providing EKG and BP output signals in response to signals provided from associated cardiac sensor(s), e.g., skin-mounted electrodes (not shown) on the patient. As can be seen in FIG. 5A the cardiac cycle monitor 121 is arranged to provide signals, via a line 133, to the controller 86, in response to the monitored cardiac cycle of the patient. The controller 86, in turn, controls the operation of the injector 50 to the delivery instrument 26 in coordination with the sensed cardiac cycle. Thus, the controller 86 can be used to initiate operation of the system to deliver the flowable treatment agent(s) into the myocardium at a predetermined point in the cardiac cycle.

If angiographic placement of the delivery instrument 26 is required, the system 20 preferably includes the heretofore identified manifold 102 as well as associated components, such as a bag of a contrast medium 123, a bag of saline 125, and a syringe 127 for delivery of a bolus of the contrast medium through the guide catheter 28 via the conduit or line 100. A blood pressure transducer 131 is also provided connected via a line 129 to the manifold. The transducer 131 provides blood pressure signals to the monitor 121.

Figure 5B:
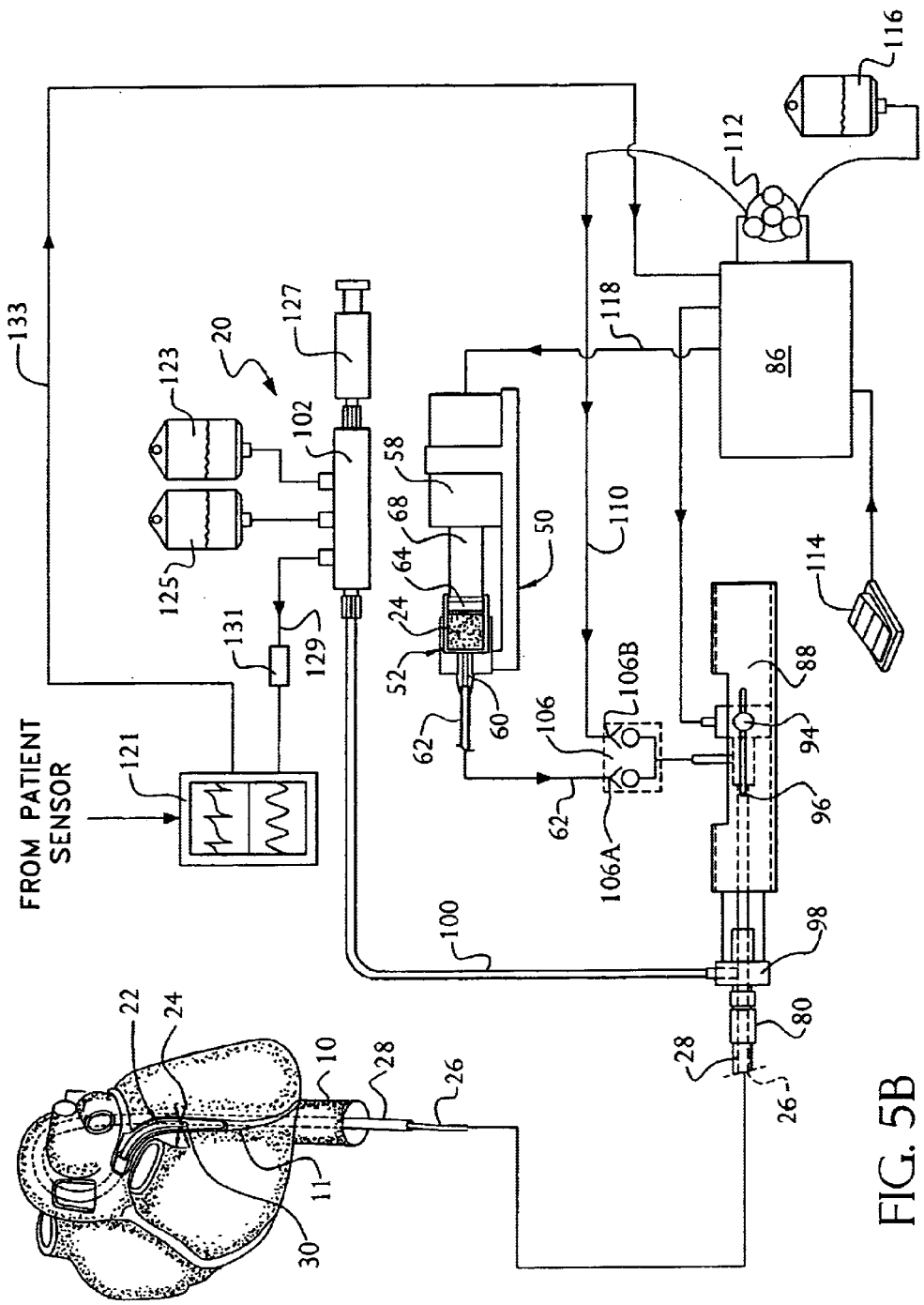
FIG. 5B is a schematic diagram and system illustration similar to that of FIG. 5A, but showing an embodiment of the entire targeted tissue system making use of the delivery instrument of FIG. 1 for delivering the flowable agent(s) into a portion of the myocardium via a coronary artery to thereby effect myocardial vascularization.

In FIG. 5B there is shown an illustration of a system for deploying the flowable agent(s) 24 into the wall of a coronary blood vessel, such as the left anterior descending (LAD) artery 11. Thus, the illustration in FIG. 5B is identical to that as shown in FIG. 5A except for the positioning of the guide catheter 28 and the delivery instrument 26 in the left anterior descending coronary artery of the heart.

In this application, the delivery instrument 26 is passed through the guide catheter 28 to the LAD where it distributes the flowable agent(s) 24 into the wall of the LAD by ejecting the agent(s) at a high velocity. This is accomplished by the combination of pressure and the rotary centrifugal action of the working head. To that end, the instrument 26 is inserted into the guide catheter 28 and moved to a location just inside the guide catheters distal tip under fluoroscope vision. The operator of the system then depresses the foot control switch 114 to the first position, whereupon nitrogen flows to the turbine 82 which in turn rotates the working head 30 at the distal tip of the instrument. The operator then advances the instrument longitudinally by sliding the knob 94 in the slot in the cradle until the working head is advanced to the appropriate location in the vessel. The foot switch 114 may then be depressed in the second position, whereupon the capsule ejector ram 68 is driven smartly into the capsule, thereby causing the needle to pierce into the capsule so that the agent(s) 24 flows through the tubing 62 into the input 106A of the highest wins valve 106 and from there through the outlet tube into the interior of the instrument 26. The instrument is then delivered down the instrument to the instrument's working head either by continued motion of the injector (assuming the capsule charge is large enough) or is carried forward by the continuing flow of saline from the peristaltic pump 112. In any case, the flowable material is forced out in a somewhat radial direction, such as shown by the arrows in FIG. 5B whereupon it passes through the artery wall and into the contiguous tissue of the myocardium.

Figure 6:
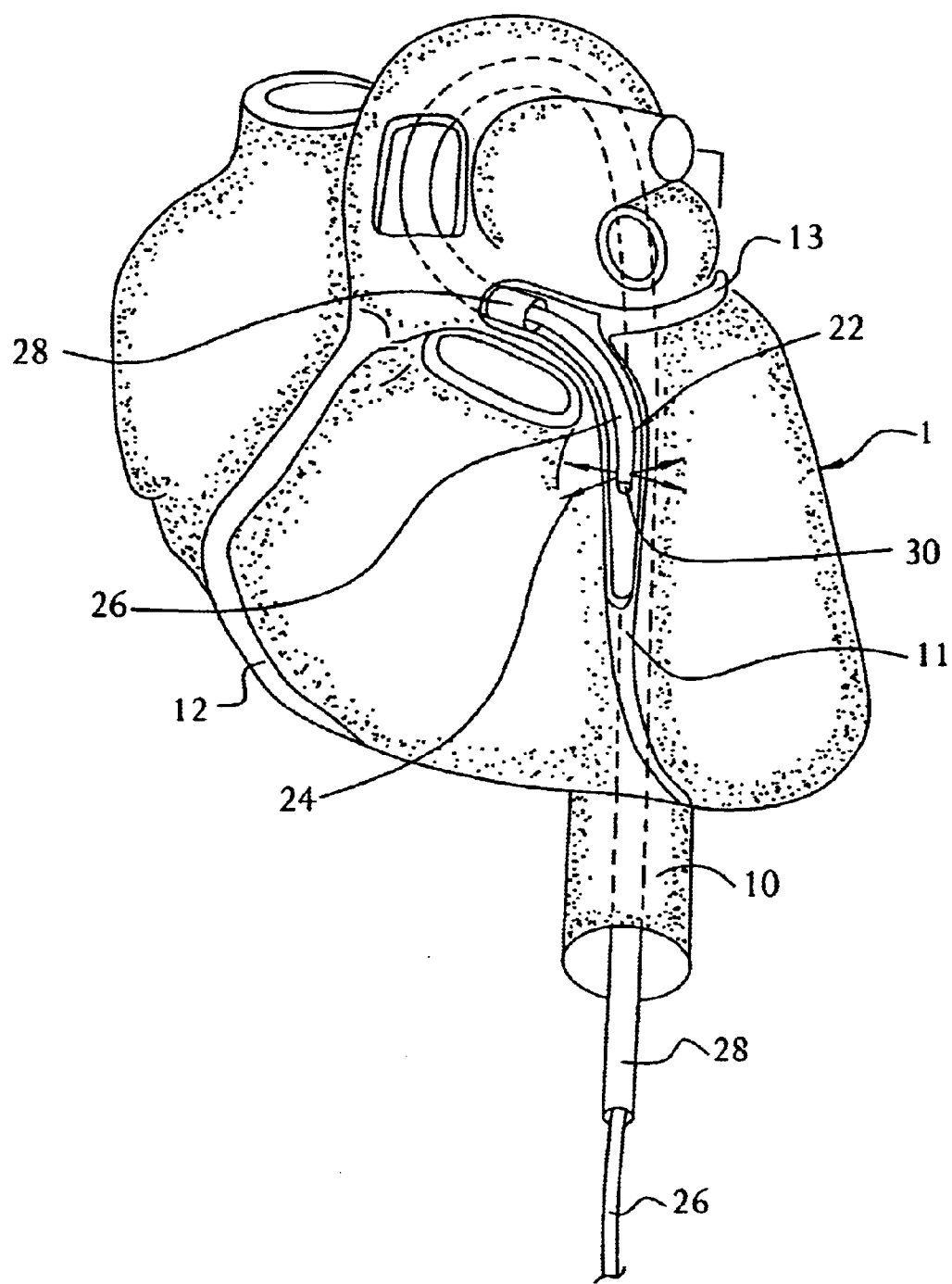
FIG. 6 is an enlarged illustration of the heart of a living human being, partially in section, showing a portion of the delivery instrument of FIG. 5B being used to deliver the flowable agent(s) into the myocardium via a coronary artery.

FIG. 6 is an enlarged portion of the illustration shown in FIG. 5B. Thus, it can be seen that when the delivery instrument is located so that it is within the desired coronary artery, e.g., the left anterior descending (LAD) artery 11, its distal end portion extends beyond the distal end of the guide catheter and lies approximately centered within the artery and parallel to the longitudinal axis thereof. Operation of the instrument 26 causes the tip to bombard the surrounding tissue with the propelled fluids (e.g., the agent(s) 24 with or without saline or other flowable materials at a high pressure). This action forces the flowable liquids into and through the artery wall and into the immediately adjacent myocardium tissue. This is achieved by increasing the local dynamic or hydrostatic pressure induced by the injected flowable materials and/or the movement, e.g., rotation, of the working head. The construction of the instrument allows the flowable agent(s) to be delivered and dispersed into a significant volume of cardiac tissue. As will be described in considerable detail later, the flowable materials or agents may be in the form of fine particulates, e.g., microspheres, which, when dispersed into the cardiac tissue cover a relatively wide area, yet are resistant to further migration, thereby retaining their beneficial effect within the desired portion of the heart.

Figure 7:
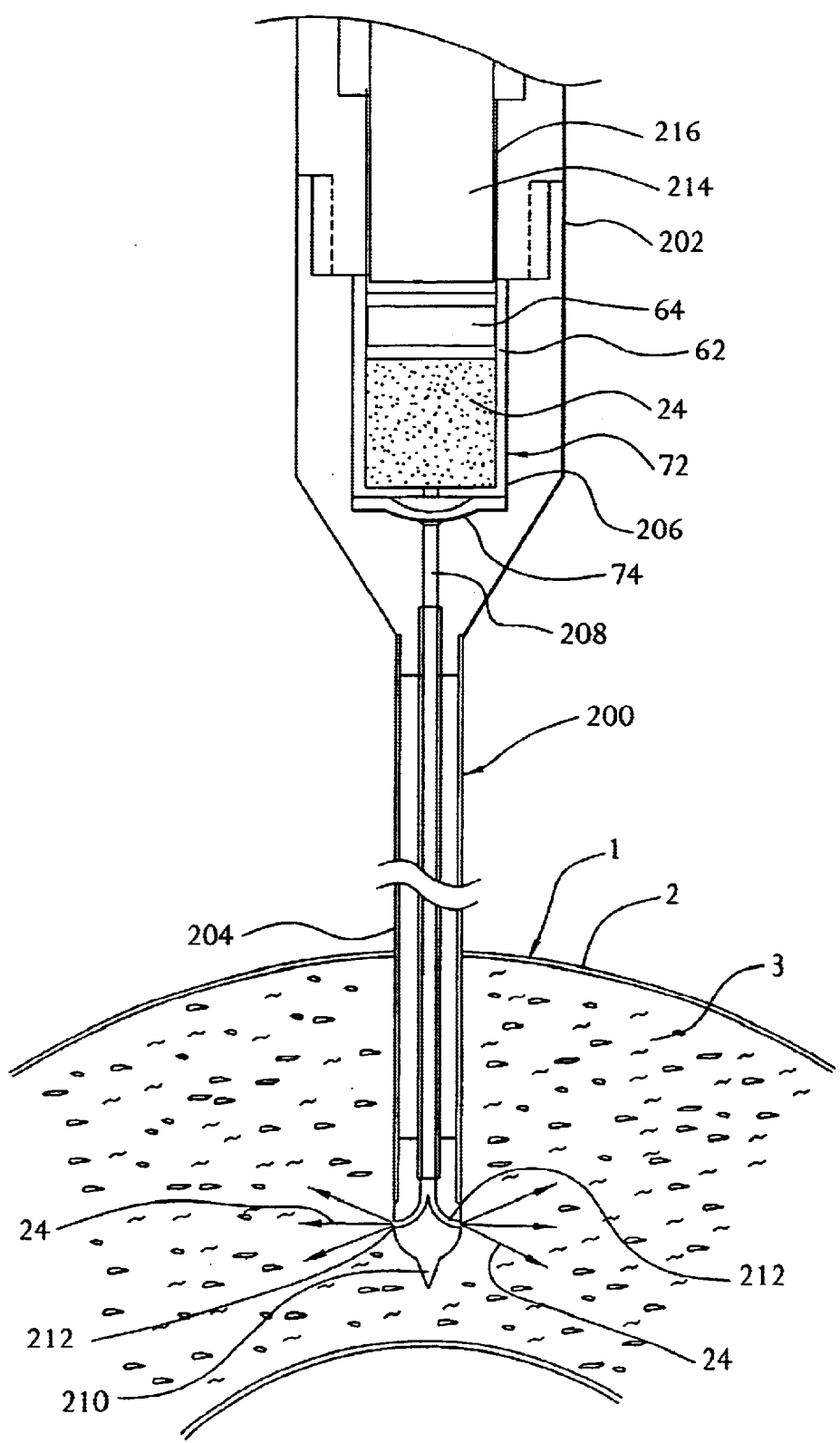
FIG. 7 is a side sectional view of one embodiment of an alternative, e.g., a rigid, delivery instrument of the targeted tissue treatment system of this invention shown being used for effecting myocardial revascularization by piercing the epicardium to create a channel in the myocardium, and deliver the flowable agent(s) therein by pressurizing the agent(s)

FIG. 7 is an illustration of a portion of the heart of a living human being, shown partially in section and showing an alternative embodiment of the delivery instrument of the subject invention for introducing the flowable agent(s) 24 therein. In the embodiment shown in FIG. 7, the delivery instrument is designated by the reference number 200 and is in the form of a jet injector. The instrument is used to deliver into the myocardium the flowable materials via the epicardium. To that end, the instrument utilizes a pressurized stream of fluid to distribute the flowable agent(s) into the targeted tissue.

The use of pressurized fluids for medical applications has been known for some time for various applications. For example, pressurized fluids have been used in the past to ablate and remove substances from the body. See for example U.S. Pat. No. 1,902,481 (Pilgrim). This patent discloses the use of a pressurized fluid or medicant to flush undesirable substances from body cavities of animals. U.S. Pat. No. 3,930,505 (Wallach) discloses a surgical apparatus for the removal of tissue from the eye of a patient by making use of a low pressure, e.g., 15 to 3500 psi jet, to disintegrate that tissue. Particles, such as salt crystals, may be introduced into the jet. A suction pump is used for material removal. U.S. Pat. No. 4,690,672 (Veltrup) discloses a low pressure, e.g., less than 450 psi water jet for ablating deposits. A vacuum pump is also used for evacuation of the fragmented material which is ablated. U.S. Pat. No. 5,496,267 (Drasler) discloses a device for the ablation and removal of thrombus deposits from tissue walls of patients by means of a high pressure jet, e.g., 5,000 to 50,000 Psi. The device of that patent may be used to infuse drugs, inject contrast media for visualization and flush the vessel. U.S. Pat. No. 5,037,432

(Molinari) discloses an apparatus utilizing pressurized fluid in conjunction with an abrasive reducing substance for removing surface portions of human tissue. The device allows a controlled application of a reducing substance for the purpose of obtaining a superficial abrasion of surface portions of the human tissue. This patent does not contemplate utilizing the system for a surgical or percutaneous tool, nor the delivery of a substance into the tissue.

The delivery instrument 200 shown in FIG. 7 is arranged to drive the flowable agent(s) 24 at high pressures into the myocardium and thus implant the agent(s) at some significant distance from the instrument's distal end 202, as indicated by the arrows in this figure. The instrument 200 is a generally rigid or partially rigid device for use in open heart surgery or for use in mini-open heart surgery through a thoracotomy. Like the instrument 26 described heretofore, the delivery instrument 200 is arranged to drive the flowable agent(s) 24 at high pressures into the myocardium 3 to thereby implant that agent at some significant distance from the instrument's distal or working end. However, unlike the delivery instrument 26 (which is threaded through the vascular system to a position so that its working head 300 is extended into the ventricle or through a coronary artery to be adjacent the site into which the flowable material will be introduced into the myocardium), the instrument 200 is arranged to penetrate the myocardium directly from the epicardium to introduce the flowable agent.

As best seen in FIG. 7 the delivery instrument 200 basically consists of two main portions, namely, a flowable agent capsule receiving portion 202 and an elongated injector tip portion 204. The capsule receiver portion 202 is in the form of an elongated body which is particularly suited to be grasped in the hand of the user. The body forms the proximal end of the instrument 200. The injector tip portion 204 is an elongated, small diameter, e.g., 1 mm, member which extends from the distal end of the body portion 202 to thereby form the distal end of the instrument. The receiver portion 202 is a generally hollow member having a cavity 206 for receipt of a rupturable capsule, like capsule 72 described heretofore. The outlet of the capsule 72 is in communication with a passageway 208 in the form of a metal tube of small bore, e.g., 0.015 inch, which extends down through the injector tip 204 to the distal end 210 thereof. As can be seen, the distal end of the tip is pointed to form a piercing member. A plurality of outlet ports 212 are provided in the distal tip and are in fluid communication with the passageway 208. The ports are equidistantly spaced about the periphery of the tip and are directed radially outward therefrom. The ports are arranged to allow the flowable agent(s) 24 to exit the instrument 200 in the form of plural, radially outwardly directed, high pressure fluid jets which are shown graphically by the arrows 24 in FIG. 7.

The delivery instrument 200 illustrated in FIG. 7 only shows the flowable agent(s) 24 delivered to the myocardium 3 in one area. However, it should be appreciated that the instrument may be positioned at different levels in the myocardium to deliver the flowable agent(s) into the entire depth of the myocardium. Further still, the distal portion 204 of the instrument 200 may include a plurality of ports 212 at different longitudinal positions therealong to distribute the flowable agent(s) into the myocardium at various levels with a single delivery or penetration.

In order to propel the flowable agent(s) out of the capsule to form those jets, the instrument 200 includes a fast acting plunger assembly. In particular, the assembly comprises a plunger 214 located immediately proximally of the piston 64 at the proximal end of the capsule 72. The plunger is located within a bore 216 in the body portion 202. A powerful spring, not shown, forming a portion of the plunger assembly is located proximally of the plunger and is normally held in a retracted, loaded position by a trigger mechanism, not shown. When the trigger mechanism is actuated by the user, it releases the spring to advance the plunger rapidly through the bore in the distal direction to engage and move the piston distally. The rapid distal movement of the piston pressurizes the agent 24 within the capsule to cause the capsule wall to burst and thereby enable the flowable agent to flow down the passageway 208 to the ports 212 where it exits in plurally radially directed high pressure jets.

It should be pointed out that the delivery instrument 200 can be constructed in accordance with the teachings of U.S. Pat. No. 2,398,544 (Lockhart) or any other prior art injector device using springs or other mechanisms for driving an agent from a capsule or receiver located therein.

In any case, the sizing of the parts of the instrument is preferably selected so that pressures of several thousand psi can be generated by the actuating mechanism, e.g., plunger and capsule combination. Such pressures are more than adequate to drive the flowable agent(s) jets a significant distance into the penetrated tissue, e.g., the myocardium.

To expedite the vascularization of cardiac tissue, the tip 210 of the device 200 is preferably pointed so that it may penetrate into the cardiac tissue a limited distance, e.g., 1–20 mm, such as shown in FIG. 7. Once it is at the appropriate depth, the agent 24 may then be pressurized and forced into the tissue through the ports 212 as described earlier. Depending on the application, one or plural penetrations can be undertaken.

In some applications, a depth control means (to be described later) may be provided to limit the depth of penetration of the distal or working end of the instrument 200 into the myocardium to disperse the flowable agent(s) into the contiguous tissue. Such depth control means may comprise means to limit the depth of the lumen(s) created by the delivery instrument, or may comprise means on an insert (to be described later) which is implanted into the targeted tissue to limit its depth of penetration into the lumen or may be a combination of both. The depth control means of the delivery instrument may be adjustable to vary the depth of the lumen(s) created by the instrument. The optimal lumen depth created by the instrument may be determined before the procedure or during the procedure by measuring the thickness of the cardiac tissue with a transesopheageal echocardiogram probe, ultrasound probe, or other measuring instrument.

It should be pointed out at this juncture that while the delivery instrument 200 is shown making use of a rupturable capsule 72, like that described heretofore, it should be clear that the instrument can make use of other types of capsules, such as the needle-puncturable capsule 52 described earlier, for holding the flowable agent(s). In such an alternative arrangement, a piercing needle 60, like that described heretofore, is provided in the injector located proximally of and in communication with the metal tube 208. The needle is directed towards the cavity holding the capsule so that it can pierce the end wall of the capsule when the capsule is moved into the point of the needle by the distal movement of the piston 64.

It should also be pointed out at this juncture that the flowable agent can include a flowable carrier material if desired. The flowable carrier material can be arranged to harden slightly after placement, like epoxy or silicon caulking material, so that it is not extruded from the cardiac tissue after penetration during the cardiac contraction cycle. As will be discussed later, a significant feature of the subject invention is the stimulation of a foreign body reaction and healing response in the myocardium which results in the formation of capillaries at the site of and adjacent the implanted flowable agents.

Figure 9:
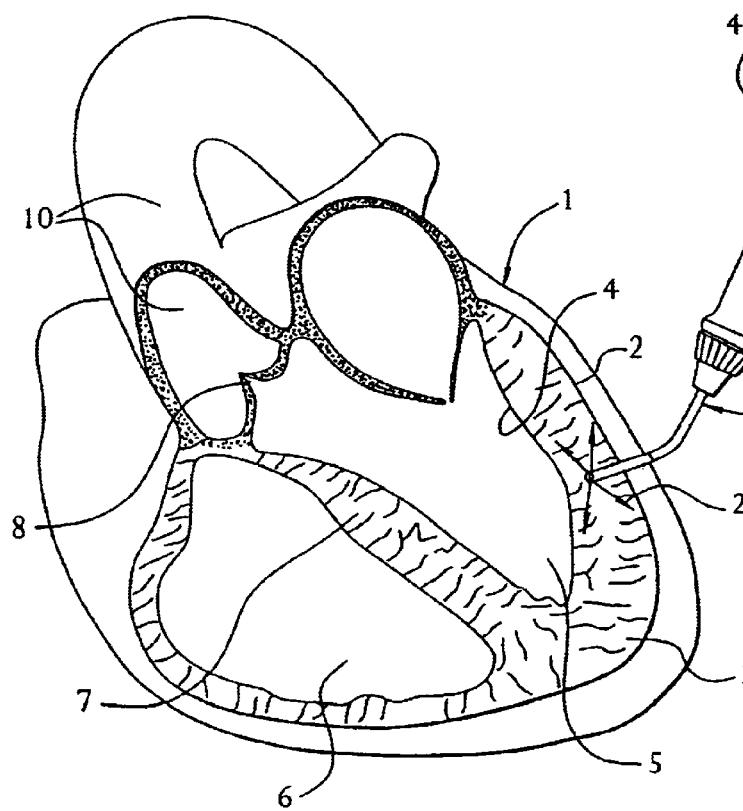
FIG. 9 is an illustration of the heart of a living human being, partially in section, showing another alternative embodiment, e.g., a vibratory, delivery instrument of the targeted tissue treatment system of this invention shown being used to penetrate a portion of the epicardium and myocardium to deliver the flowable agent(s) into the myocardium.

FIG. 9 is an illustration of the heart of a living human being, partially in section, showing one embodiment of another flowable agent(s) delivery instrument 400 forming a portion of a targeted tissue treatment, e.g., myocardial revascularization, system of the subject invention. In this case, the instrument is a vibratory device which is used to penetrate a portion of the epicardium 2 and then into the myocardium 3 to deliver the flowable agent(s) into the myocardium. Vibratory energy provided by this embodiment may be sonic, ultrasonic or other energy used to create channels or lumens in the targeted tissue into which the flowable agent(s) 24 will be ejected or deposited for dispersion into tissue contiguous with the lumen or channel into which it is introduced. Alternatively, the deployment instrument 400 can provide one or more of various other types of energy to the targeted tissue to create the channels or lumens and then deliver the flowable agents therein. Examples of other types of energy contemplated for such procedure are thermal energy, mechanical energy (e.g., rotational cutting or boring, slicing, etc.), electrical energy (e.g., radiofrequency energy, etc.), hydraulic energy (e.g., pneumatic energy, radiation energy, laser or other light energy, or other types of electromagnetic energy, etc.) It should be pointed out at this juncture that the application of energy to the cardiac tissue will not only serve to create the lumens or channels but can also disable or denervate local nerves in the targeted tissue. This factor may prove particularly significant for cardiac tissue treatment applications by minimizing or otherwise reducing patient-pain resulting from angina.

In some applications, such as where the deployment instrument 400 applies electrical energy to the cardiac tissue to form the lumens or where the formations of the lumens and/or the deployment of the flowable agents therein is best accomplished during a particular portion of the cardiac cycle, the targeted tissue treatment system utilizing a vibratory instrument like instrument 400 may also include some control and sensing means (such as will be described later) that synchronizes the operation of the delivery instrument to a specific portion of the cardiac cycle.

Figure 10:
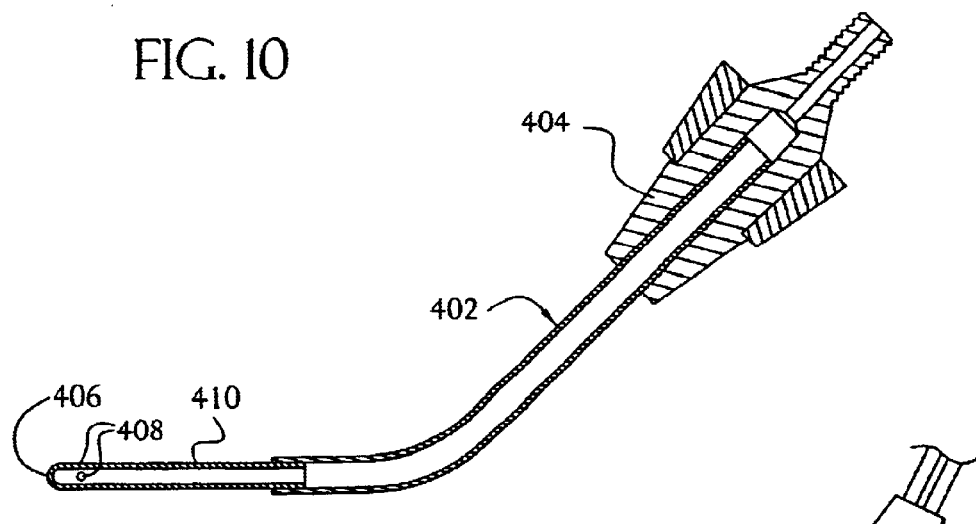
FIG. 10 is an enlarged side sectional view showing a portion of the vibratory delivery instrument embodiment of FIG. 9 for penetrating tissue and delivering the flowable agent(s) into the myocardium.

The instrument 400 as shown herein is merely exemplary. Thus, it can be of any suitable construction. For example, it can be constructed similarly to the device disclosed in U.S. Pat. No. 4,315,742 (Nash et al.) whose disclosure is incorporated by reference herein. That device basically comprises an air-powered vibratory instrument which vibrates at approximately 7 KHz. This example is not intended to exclude other means for generating vibratory energy for the instrument 400, such as magnetostrictive or piezoelectric devices. In the exemplary embodiment 400 shown herein, the device basically comprises the device of the aforementioned Nash et al. patent with an alternative tip 402 constructed in accordance with this invention and as shown in FIG. 10. In particular, as can be seen in FIG. 10, the tip 402 is an elongated angled member which is arranged to be attached to the screw thread at the distal end of the Nash et al. device. The angled tip is present within a holder 404. The free end of the tip is rounded at its distal end 406 and includes plural small radially directed outlet ports 408 for distribution of the flowable agent(s) 24. The tip may be of a continuous tapered form (not shown) or a step form having a reduced diameter distal section 410 including the free end 406 as shown in the illustration of FIG. 10. The fact that the distal end of the tip is of reduced diameter coupled with the fact that it is located a distance from the holder 84 serves to amplify the vibration produced by the instrument during operation. The flowable agent 24 is provided by the instrument 400, as will be described later, and exits from the plural ports 408 in the form of plural radially directed outward jets as shown by the arrows in FIG. 9.

Figure 11:
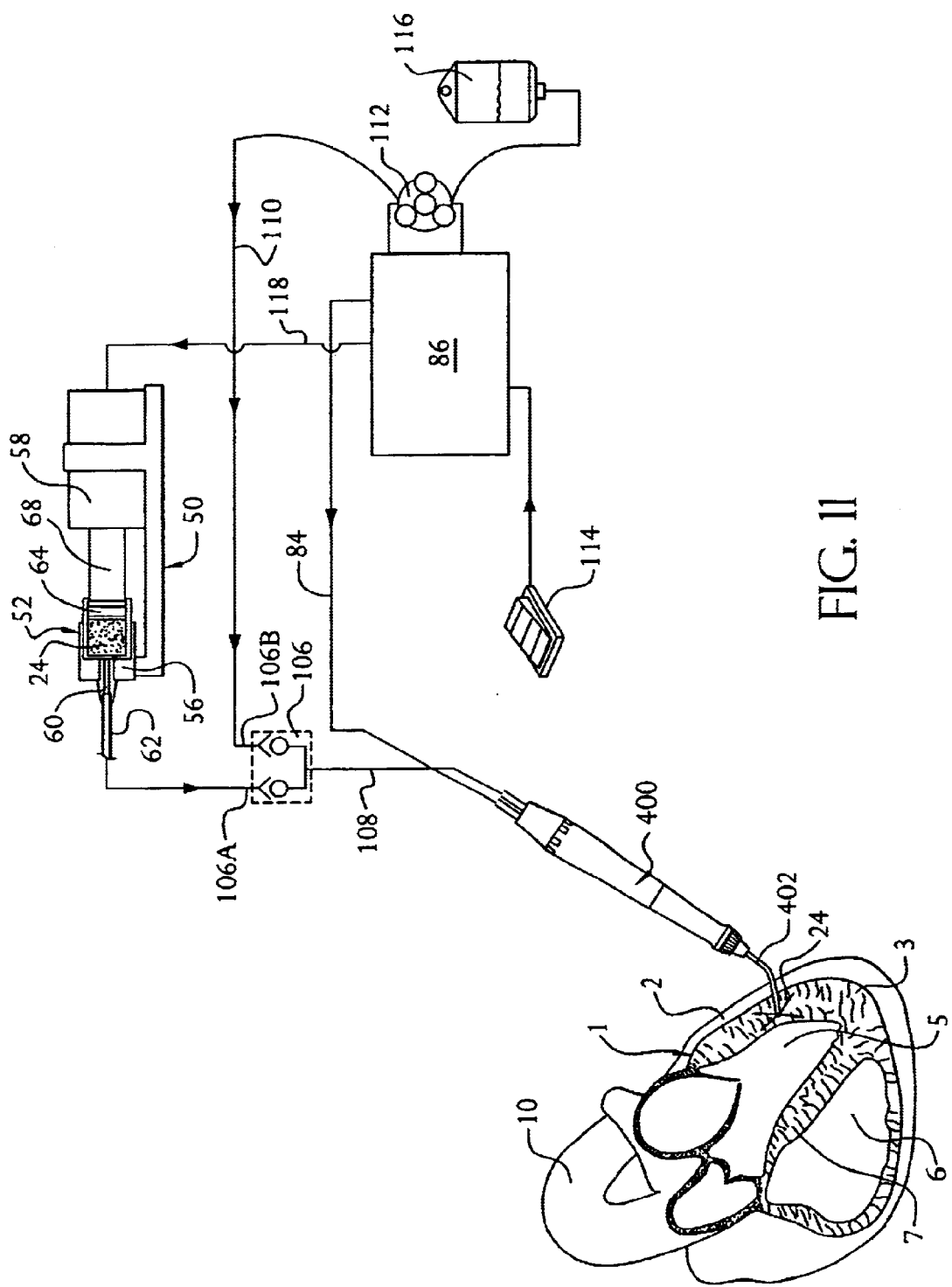
FIG. 11 is a schematic diagram and system illustration showing another embodiment of a targeted tissue treatment system of this invention including the embodiment of the vibratory delivery instrument illustrated in FIG. 9 being used to penetrate and deliver the flowable agent(s) to a portion of the myocardium via the epicardium.

FIG. 11 shows a complete targeted tissue treatment system 20 making use of the vibratory delivery instrument 400 just described to effect the vascularization of the myocardium. Thus, as can be seen, the free end 406 of the tip 402 of the instrument 400 is placed against the epicardium and the foot control switch 114 is depressed to the first position. Nitrogen gas passes through the tube 110 directly to the instrument 400 thus generating vibrations in the tip 402. Concurrently, saline flows from the bag 116 through the pump 112 to the input 106B of the highest wins valve 106 and from there through the feed line 108 into the interior of the instrument 400. The saline flows through the instrument to the tip and out through the ports 408. This action bores a channel or lumen through the epicardium into the myocardium. When this has been accomplished, the foot switch is then depressed to the second position, whereupon the capsule injector ram 68 of the system 20 is driven smartly into the capsule 52, thereby ejecting the flowable agent(s) 24 through the highest wins valve port 106A into the feed tube 108. The agent(s) 24 is delivered through the instrument 404 to its tip 402 either by continued motion of the injector (assuming the capsule charge is large enough) or carried forward by the continuing flow of saline from the pump. The flowable agent thus is driven into the myocardium by the use of pressure alone or by the vibration of the instrument alone or by a combination of both.

Figure 12:
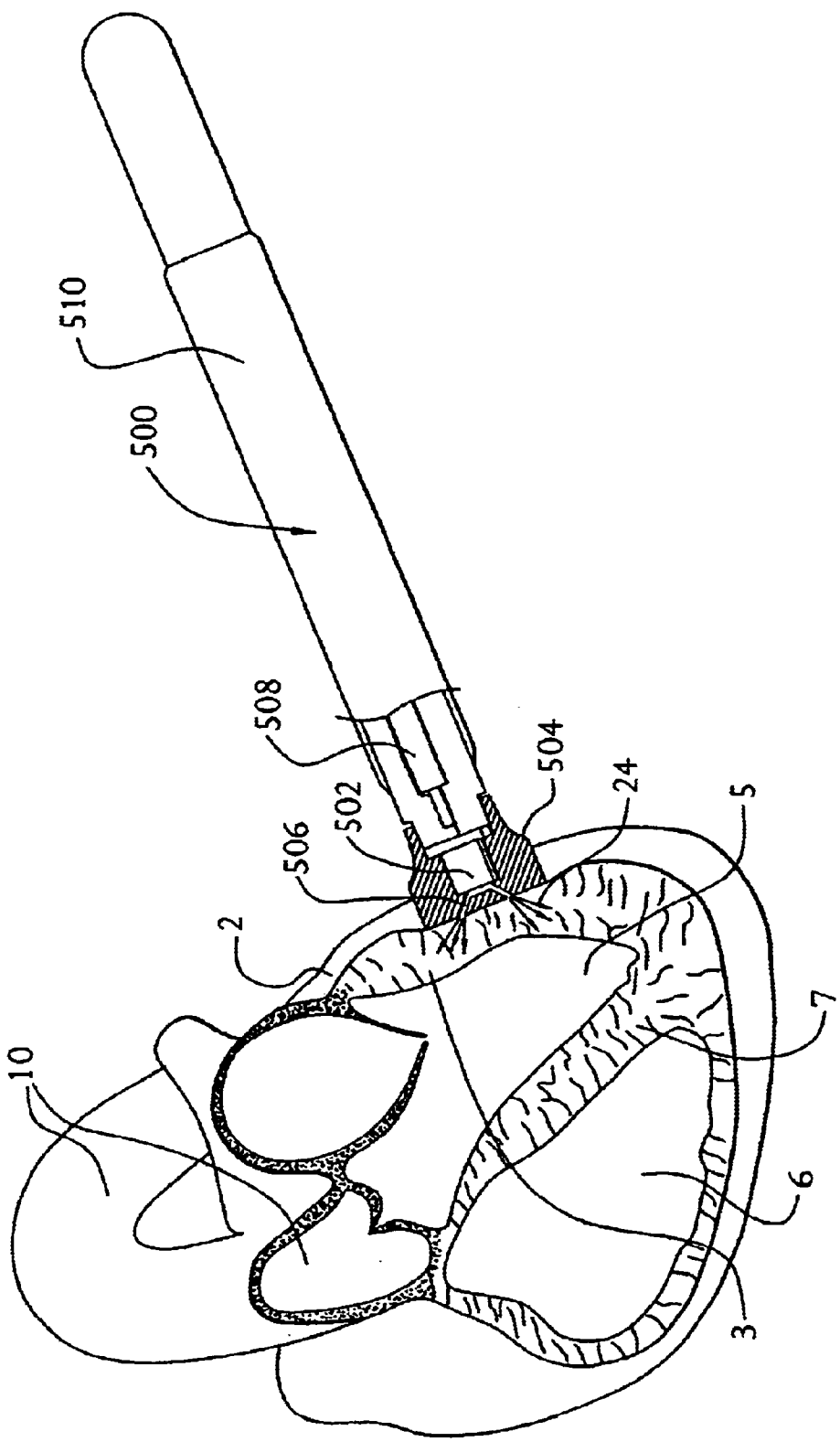
FIG. 12 is an illustration of the heart of a living human being, partially in section, showing one embodiment of an alternative delivery instrument forming a portion of the myocardial revascularization system of the subject invention being used to deliver the flowable agent(s) into the myocardium via the epicardium.

FIG. 12 is an illustration, not to scale, of the heart of a living human being, shown partially in section, and illustrating an embodiment of another alternative flowable agent (s) delivery instrument (not to scale) forming a portion of a targeted tissue, e.g., myocardial revascularization, system of the subject invention. This embodiment is denoted by the reference number 500 and basically comprises a jet injector which is used to deliver the flowable agent(s) 24 as a pressurized stream into the myocardium 3 via the epicardium 2.

As is known, pressurized fluids have been used in the past in jet injector devices for administering intramuscular and subcutaneous medications to a patient through the patient's skin, without the use of a skin-penetrating needle. The advantages of such systems include the reduction of pain and apprehension associated with needle injections, the elimination of needle-stick injuries, and the reduction of environmental contamination associated with needles. Jet injection devices have been considered for immunization vaccines, hormone delivery, local anesthetics, and insulin delivery. For example, U.S. Pat. No. 2,398,544 (Lockhart) discloses a hypodermic injector for administering a liquid through the skin of a living being without the necessity of having a needle puncture the skin. The device uses a pressure of 8,000 to 10,000 psi to force a stream of a liquid through the skin. U.S. Pat. No. 2,737,946 (Hein) discloses an apparatus for hypodermically injecting medicants through the skin without the use of a penetrating needle. U.S. Pat. No. 2,762,370 (Venditty) discloses a needleless hypodermic injector for use in discharging liquid medicants from an orificed ampule in the form of a minute stream. An initial high-pressure discharge causes the jet stream to distend the skin and force the liquid to a predetermined depth beneath the surface. After the minute opening in the epidermis has been produced, the pressure of the stream is immediately reduced to a lower second stage for completing transfer of the remaining liquid from the ampule. U.S. Pat. No. 2,800,903 (Smoot) discloses a device for the injection of a medicant without the use of a long needle. U.S. Pat. No. 5,704,911 (Parsons) discloses a system utilizing hypodermic jet injections to deliver liquid medicants without piercing the skin with a needle. U.S. Pat. No. 4,165,739 (Doherty et al.) and U.S. Pat. No. 3,815,514 (Doherty) disclose innoculators for injecting a fluid through the skin without the use of a needle.

Referring now to FIG. 12, it can be seen that the jet injector delivery instrument 500 as illustrated is constructed similarly to the inoculation injector described in U.S. Pat. No. 2,398,544 (Lockhart) whose disclosure is incorporated by reference herein. This construction is referred to since it is illustrative of some forms of devices that are suitable for the purpose of injecting a flowable agent into a targeted tissue, e.g., the myocardium, under high pressure. Other types of jet injectors could be utilized in accordance with this invention.

As can be seen clearly in FIG. 12, a capsule 502 containing a flowable agent(s) constructed in accordance with this invention is held within a dispensing chamber in a cap portion 504 of the jet injector instrument 500. The cap includes multiple tiny orifices 506 arranged in a pattern, e.g., equidistantly spaced and slightly flared outward, to give a wide spread to the injected agent(s) 24 within the myocardium. Alternatively, the injector device may only include a single orifice for injecting a single jet stream of the agent into the myocardium. In the embodiment shown, the instrument 500 includes an activatable plunger 508 which is arranged to be released by axial motion of a sleeve 510 to rapidly engage or push into the capsule 502. This action propels the flowable agent(s) 24 of the capsule through the orifices 506 in the cap 504 and into the contiguous cardiac tissue, i.e., through the epicardium and into the myocardium as shown by the arrows in FIG. 12.

It should be pointed out at this juncture that the instrument 500 may be constructed differently. For example, the instrument 500 could consist of a local jet holder, like cap 504, but with the pressure source and capsule remote from the tip.

During the operation of the system of FIG. 12, the agent or carrier fluid for the agent (to be described later) intended for introduction into the targeted tissue is inserted in a proper dosage into the dispensing chamber. As discussed previously, pre-dosed capsules can be utilized. In any case, the plunger is driven forward by the linearly applied force and converts this force into pressure on the flowable agents. The force is sufficient to cause the flowable agents to exit the chamber via the orifice(s) 506 at such a velocity that they can be hypodermically injected into the injection site. It is possible that an ampule or other agent reservoir could be used and as such the ampule could utilize a dosage scale or graduations for use in metering proper doses. Moreover, it is conceived, but not illustrated, that an embodiment of a needleless hypodermic injection delivery instrument of this invention would include an ampule assembly having a chamber for holding the flowable agent(s), e.g., a liquid suspension, and an injector for receiving and mounting the ampule assembly. In such a case, the ampule assembly will have an opening at an end of an ampule shell through which the flowable agent can be drawn into an ejected out from. A plunger assembly movable within the chamber is used for drawing the flowable agent into the chamber and for injecting the material out of the chamber. The injector applies a force that activates a plunger to thereby force the material to leave the chamber via the orifice(s) at a velocity sufficient that the agent can be hypodermically injected into the targeted tissue. The force may be applied by a firing mechanism that releases compressed gas from a storage compartment. The compressed gas acts upon a piston which drives the plunger to subsequently eject the preselected dosage of the flowable agent(s) through the orfice(s) at the distal end of the instrument. A shock absorber may be used to soften or cushion the shock of the triggering mechanism. For some flowable agents, e.g., vaccines, there may be a standard implant dosage, while for other agents there may be variable size dosages, e.g., weight dependent medications. Safety interlocks, not shown, can be incorporated to prevent system activation until the delivery instrument is fully secured in position.

Figure 13:
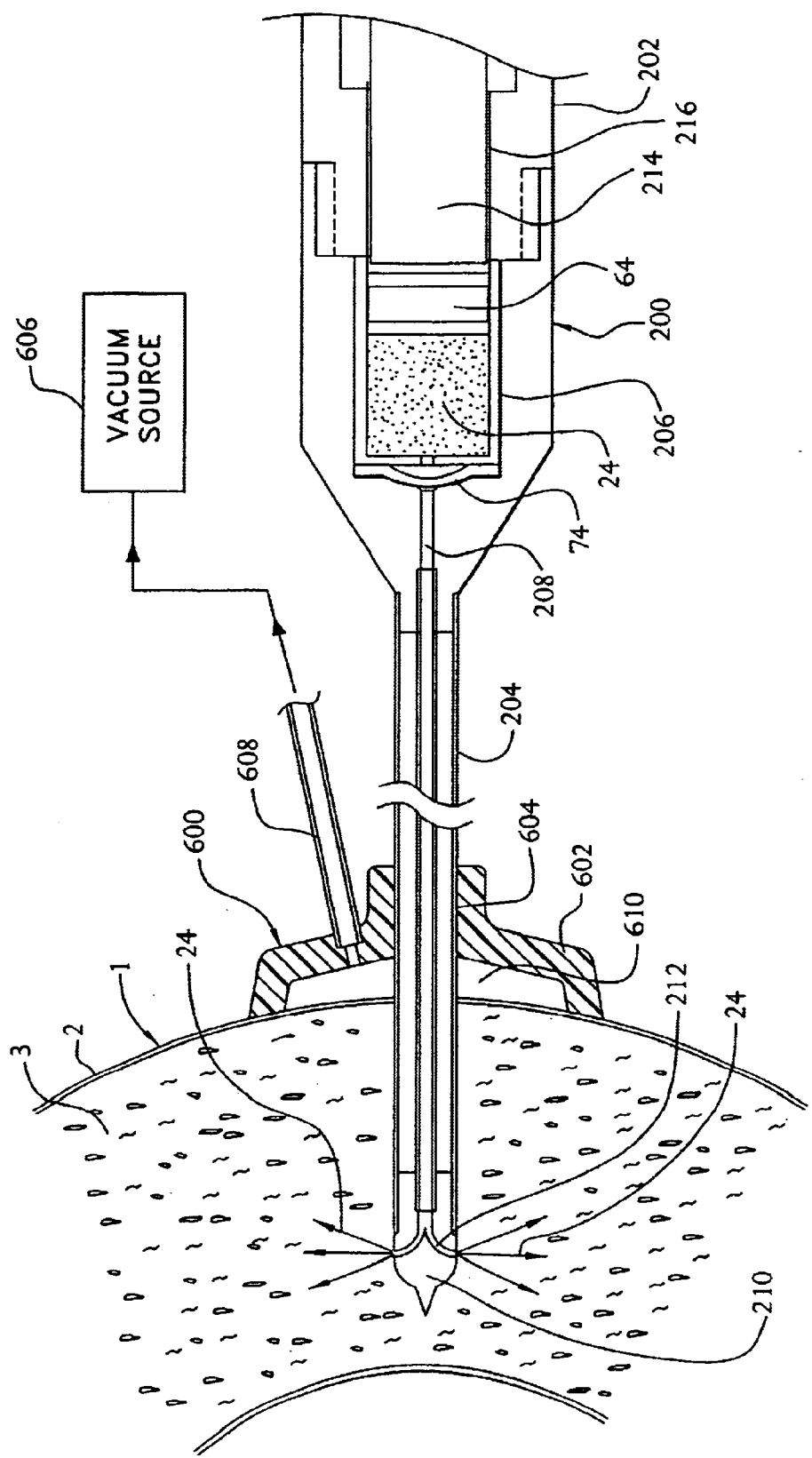
FIG. 13 is a side sectional view of the embodiment of the delivery instrument of FIG. 7 with a stabilizing device, e.g., a suction hood, associated with it and shown being used to pierce the epicardium to create a channel in the myocardium and to deliver the flowable agent(s) into the channel in the myocardium.

In some applications it may be desirable to stabilize the flowable agent(s) delivery instrument against the targeted tissue, e.g., the endocardium or epicardium during the tissue treatment, e.g., revascularization, procedure. For such applications, the system 20 may make use of some releasable securement or attachment means, like that shown in FIG. 13. That means basically comprises a suction hood, to be described in detail later, which stabilizes or otherwise holds the flowable agent delivery instrument in place. Once positioned, the delivery instrument can be activated to direct the flowable agent(s) therefrom into the targeted tissue. It must be pointed out at this juncture that the use of the stabilization as disclosed herein is not confined to the use with any particular type of delivery instrument. Thus, it can be used with powered, e.g., rotatable working head instruments like shown in FIG. 2, or manually driven instruments like shown in FIGS. 7, 9 and 13, to create lumens within the targeted tissue and to introduce the flowable agent(s) therein. FIG. 13 illustrates one such device when applied to the delivery instrument of FIG. 7. Thus, referring now to FIG. 13, there is shown a delivery instrument 200 of FIG. 7 but including a releasably securable attachment mechanism 600 in the form of a suction hood 602 assembly and associated components. The suction hood assembly is slidably mounted on the distal portion 204 of the instrument 200. The suction hood assembly 602 basically comprises a cup-shaped hollow member formed of a resilient material, e.g., silicone rubber, having a central passageway 604 therein for accommodating the distal end portion 204 of the delivery instrument 200 (or any other delivery instrument). The periphery of the cup-shaped member is in the form of an enlarged flange which is arranged to directly engage the epicardium or other targeted tissue. A source of vacuum 606 is provided coupled to the proximal end of a tube 608 in communication with the interior of the cup-shaped hood. The vacuum source 606 is arranged to be actuated by the operator of the system via any suitable means (not shown). This action couples the vacuum source 606 to the interior 610 of the hood to produce suction at the distal end of the hood thereby holding it in place on the targeted tissue, e.g., epicardium, centered over the location at which the delivery instrument 200 is to enter the underlying tissue. The operator can then drive the instrument 200 inwardly into and through the epicardium and into the myocardium with the suction cup stabilizing the zone of interest.

Figure 8:
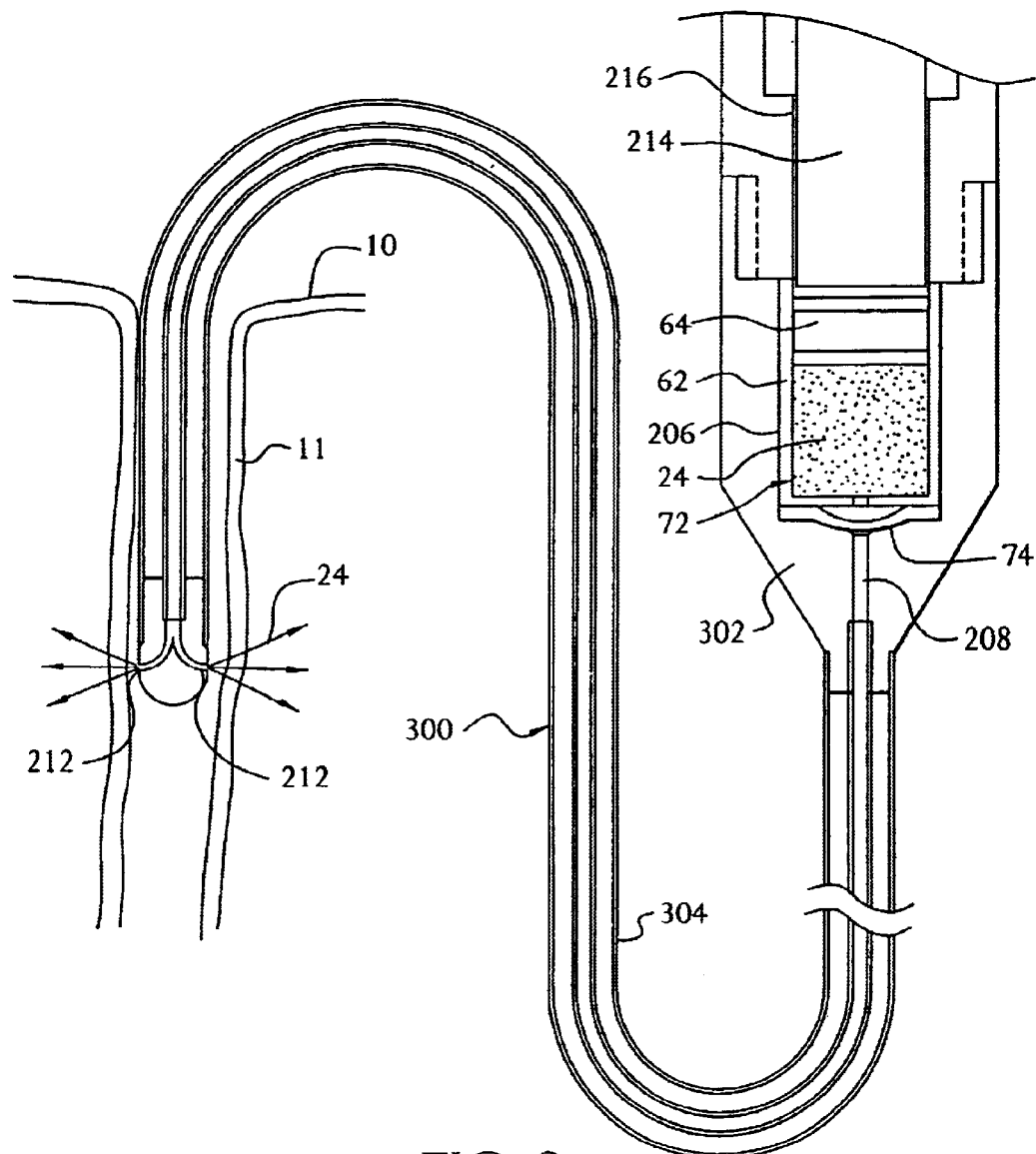
FIG. 8 is a side sectional view of one embodiment of another alternative, e.g., a flexible, delivery instrument of the targeted tissue treatment system of this invention shown being used for effecting myocardial revascularization by delivering the flowable agent(s) intravascularly through a vessel, e.g., coronary artery, wall into myocardium.

FIG. 14 shows the flowable agent(s) delivery device 300 of FIG. 8 but used in a tissue treatment application wherein the distal end portion of the instrument is fed through the urethra 14 into the prostate gland 15 of a living male being for the purpose of delivering the flowable agent(s) 24 into the prostate gland in the form of jets of that agent. The instrument 200 could thus be used to treat prostate cancer, benign prostate hyperplasia, or other prostate conditions with suitable flowable treatment agent(s), such as tissue and/or vascular antagonists. If desired, the instrument may be positioned so that its distal end is within the bladder 16 to deliver the flowable treatment agent(s) thereto for treating a tumor T.

In accordance with one preferred aspect of this invention, the flowable agent(s) is in the form of a plurality, e.g., a host or myriad, of small particles of one or more materials (the materials to be described in the tables to follow) either alone or in combination with some carrier fluid, e.g., a liquid. Preferably, the particles are in the form of microspheres or other microparticles. FIGS. 15A–15H show respective embodiments of the microparticles which may be used as the flowable agent or as part of the flowable agent or for delivering flowable agents into the tissue of a living being in accordance with this invention.

As described previously, the agents 24 are formed of at least one material that can elicit a beneficial response within cardiac or other tissues. For example, the agents can be of a pharmaceutical or genetic nature and their presence can initiate a bio-chemical/biological process that stimulates the tissue to heal itself. The agents can also trigger the onset of a foreign body or healing response to cause the formation of lumens in communication with the arterial system.

Before describing the exemplary embodiments of the microspheres shown in FIGS. 15A–15I The flowable materials may be of any particulate size from approximately 1 micron to approximately 1 mm. In FIGS. 15A–15I, the particles are shown as being microspheres or microparticles.

Referring now to FIG. 15A, it can be seen that while there is shown a single microsphere 700 which along with others can be used to form the flowable agent. The microsphere 700 basically comprises an outer layer 702 and an inner core 704. The outer and inner layers may be of different materials or contain different agents or different concentrations of the same agent. By varying the absorption rate of the different layers, the release rate of any agent stored in the material will vary accordingly. Additionally, the inner core can be an encapsulated liquid containing an agent or plural agents.

FIG. 15B shows a microsphere 706 having a matrix of small pockets of agents 708 dispersed therein. As the microsphere 706 is absorbed, the agents in the matrix are released.

FIG. 15C shows a microsphere 710 having a matrix of small pockets of agents 714 dispersed therein and which matrix is coated by a continuous shell 714. The shell can contain no agent or different agents than are contained in the interior matrix.

FIG. 15D shows a microsphere 716 having an outer layer 718 and an encapsulated liquid core 719 containing the agent(s).

FIG. 15E shows a microsphere 720 having multiple layers 722 with thin coatings of agents 724 between each layer. As the layers 722 are absorbed, the agents 724 between the layers will be released. Additionally, the thin layers may comprise a material that may not be related to the treatment of the targeted tissue; but rather is an intermediate material which connects two layers of material. For example, it may comprise a coating applied to a polymer surface that contains receptors for a specific biological material, e.g., a recombinant adenovirus expressing human fibroblast growth factor-2 (FGF-2).

FIG. 15F shows a homogeneous microsphere 726 that is evenly seeded with agents 728 throughout. The agents 728 are uniformly released as the microsphere is absorbed.

FIG. 15G shows a microsphere 730 that is coated with a thrombogenic agent 732 such as thrombin, that will promote clotting of blood around the agent to prohibit movement of the agent through the tissue after it is deposited.

FIG. 15H shows a microparticle (not a sphere, but rather an irregularly shaped body) 734 seeded with a matrix of encapsulated agents 736 throughout. The irregular shape of the body 734 tends to render it resistant to movement after it is deposited in the targeted tissue.

FIG. 15I shows a small shard or piece of a polymer 738 or some other material that could be coated or seeded with a suitable treatment agent. The irregular shape of the polymer body also serves to prevent movement of it after it is deposited in the targeted tissue.

As is know, microspheres are well known for their use in long term controlled release of drugs or other therapeutic agents. This is a highly developed technology that has been used in many applications and such microspheres are available from a variety of sources (e.g., Polymicrospheres, Indianapolis, Ind.). The microsphere structures typically consists of: (a) a continuous drug phase surrounded by a continuous barrier membrane or shell (microcapsule), (b) a shell structure where the drug phase is subdivided into numerous domains scattered uniformly through the interior of the microsphere, (c) a polymer matrix throughout which the drug is uniformly dispersed, (d) a structure where the drug is either dissolve or molecularily dispersed within the carrier material from which the microsphere is prepared, and (e) solid. The most common method of delivering drugs or other therapeutic agents with microspheres incorporates these agents uniformly within a polymer matrix.

The fabrication of and application of microspheres is well known and as such the following examples are included herein as reference. U.S. Pat. No. 3,887,699 describes a solid biodegradable polymer spheroids implants which incorporate a drug for sustained release as the polymer naturally degrades in the human body. Many different methods of constructing this type of controlled release system have been developed. Although the uniform matrix of a polymer provides a simple and efficient means of controlled release of agents with microspheres, many advanced methods of containing and releasing the therapeutic agents have been developed. U.S. Pat. No. 4,637,905 (Gardner) discloses a method for encapsulating a therapeutic agent within a biodegradable polymer microsphere. U.S. Pat. No. 4,652,441 (Okada et al.) discloses a method of utilizing a water-in-oil emulsion to give prolonged release of a water-soluble drug. The patent describes a wide variety of drugs that can be delivered via prolonged release micro-capsules as well as suitable polymeric materials and drug retaining substances. It is conceived that the system of this invention could incorporate any of the drugs described to in this patent to generate a beneficial effect in the cardiac tissue. U.S. Pat. No. 5,718,921 (Mathiowitz et al.) discloses a method for constructing a multiple layer microsphere which can release two different drugs at controlled rates or a singe drug at two different rates. U.S. Pat. No. 5,912,017 (Mathiowitz et al.) also discloses a method of forming two layered microspheres by using an organic solvent or melting two different polymers, combining them with a desired substance and cooling. Microspheres are not limited to just water-soluble therapeutic agents. See, for example, U.S. Pat. No. 5,288, 502 (McGinity et al.) which discloses a multi-phase microsphere which is capable of incorporating water-soluble and water-insoluble drugs.

Several embodiments of the subject invention utilize the incorporation of therapeutic agents into microparticles or microspheres that degrade over time and release the therapeutic agents. As a non limiting example, microparticles can be used to deliver any type of molecular compound, such as proteins, genetic materials, proteins, peptides, pharmacological materials, vitamins, sedatives, steroids, hypnotics, antibiotics, chemotherapeutic agents, prostaglandins, and radiopharmaceuticals. The delivery system of the present invention is suitable for delivery the above materials and others including but not limited to proteins, peptides, nucleotides, carbohydrates, simple sugars, steroids, pharmaceuticals, cells, genes, anti-thrombotics, antimetabolics, growth factor inhibitor, growth promoters, anticoagulants, antimitotics, and antibiotics, fibrinolytic, anti-inflammatory steroids, and monoclonal antibodies. Examples of deliverable compounds are listed in Table 1 and 2.

TABLE 1

Examples of Biological Active Ingredients

Growth factors
Genetic material
Fibroblast Growth Factor (FGF)
Adenovirus
Bone morphogenic proteins (BMP)
Hormones
Stem Cells
Vascular Endothelial Growth Factor (VEGF)
Interlukins
Insulin-like Growth Factors (e.g. IGF-I)
Platelet-derived Growth Factor (PDGF)

TABLE 2

Examples of Pharmaceutical ingredients

Thrombin
Anti-inflammatorys
Anti-proliferative agents
Immunosuppressant agents
Glycosaminoglycans
Collagen inhibitors
Anticoagulants
Anti-bacterial agents
Vasodilators
Calcium channel blockers
ACE inhibitors
Beta blockers
Antiarrhythmics
Antiplatelets
Thrombolytics Microspheres can be made of a variety of materials such as polymers, silicone and metals. Biodegradable polymers are ideal for use in creating microspheres. There are essentially three classes of biodegradable polymers: (1) water-soluble polymers rendered insoluble by hydrolytically unstable cross-linking agents, (2) water-insoluble polymers that become soluble by hydrolysis but retain their molecular backbone, and (3) water-insoluble polymers that become soluble by backbone cleavage. Polylactic Acid and Polyglycolic Acid are well known examples of resorbable polymers. The release of agents from absorbable microparticles is dependent upon diffusion through the microsphere polymer, polymer degradation and the microsphere structure. Although most any biocompatible polymer could be adapted for this invention, the preferred material would exhibit in vivo degradation. It is well known that there can be different mechanisms involved in implant degradation like hydrolysis, enzyme mediated degradation, and bulk or surface erosion. These mechanisms can alone or combined influence the host response by determining the amount and character of the degradation product that is released from the implant. The most predominant mechanism of in vivo degradation of synthetic biomedical polymers like polyesters, polyamides and polyurethanes, is generally considered to be hydrolysis, resulting in ester bond scission and chain disruption. In the extracellular fluids of the living tissue, the accessability of water to the hydrolysable chemical bonds makes hydrophilic polymers (i.e. polymers that take up significant amounts of water) susceptible to hydrolytic cleavage or bulk erosion. Several variables can influence the mechanism and kinetics of polymer degradation. Material properties like crystallinity, molecular weight, additives, polymer surface morphology, and environmental conditions. As such, to the extent that each of these characteristics can be adjusted or modified, the performance of this invention can be altered.

Finally, many biodegradable polymers are also used to construct these microspheres such as polylactide, polylactide, copolymers with glycolides, lactides and/or epsilon-caprolactone, polyanhydrides, polyorthoesters, and many others. The polymers of poly (d,l-lactic acid) and poly (d,l-lactic) co-glycolic acid are among the most preferred polymers used historically for controlled release. However, virtually any biodegradable and/or biocompatible material may be used with the present invention. A list of example biocompatible materials are shown in Tables 3 and 4.

TABLE 3

Biodegradable Polymer Examples

Polyglycolide (PGA)
Polylactide
Copolymers of glycolide
Glycolide/L-lactide copolymers (PGA/PLLA)
Glycolide/trimethylene carbonate copolymers (PGA/TMC)
Polylactides (PLA)
Poly-L-lactide (PLLA)
Poly-DL-lactide (PDLLA)
L-lactide/DL-lactide copolymers
Lactide/tetramethylglycolide copolymers
Lactide/trimethylene carbonate copolymers
Lactide/σ-valerolactone copolymers
Lactide/ε-caprolactone copolymers
Polydepsipeptides
PLA/polyethylene oxide copolymers
Poly-β-hydroxybutyrate (PBA)
PHBA/γ-hydroxyvalerate copolymers (PHBA/HVA)
Poly-β-hydroxypropionate (PHPA)
Poly-p-dioxanone (PDS)
Poly-σ-valerolactone
Poly-ε-caprolactone
Methyl methacrylate-N-vinyl pyrrolidone copolymers
Polyesteramides
Polyesters of oxalic acid
Polydihydropyrans
Polyalkyl-2-cyanoacrylates
Polyurethanes (PU)
Polyvinyl alcohol (PVA)
Polypeptides
Poly-β-malic acid (PMLA)
Poly-β-alkanoic acids
Trimethylene carbonate
Polyanhydrides
Polyorthoesters
Polyphosphazenes
Poly (trimethylene carbonates)
PLA-polyethylene oxide (PELA)
Tyrosine based polymers

TABLE 4

Examples of other suitable materials

Alginate
Calcium
Calcium Phosphate
Ceramics
Cyanoacrylate
Collagen
Dacron
Elastin
Fibrin
Gelatin
Glass
Gold
Hydrogels
Hydroxy apatite
Hydroxyethyl methacrylate
Hyaluronic Acid
Liposomes
Nitinol
Oxidized regenerated cellulose
Phosphate glasses
Polyethylene glycol
Polyester
Polysaccharides
Polyvinyl alcohol
Platelets, blood cells
Radiopaque
Salts
Silicone
Silk
Steel (e.g. Stainless Steel)
Synthetic polymers
Thrombin
Titanium It must be pointed out at this juncture that the agents of this invention are preferably configured such that their presence in the myocardial tissue does not significantly limit the contractility of the cardiac muscle. As previously described, the agents may be coated with or contain growth factors, anti-oxidants, seeded cells, or other drug/biologically active components depending upon the result desired.

The main feature of these constructions is to stimulate a foreign body reaction and a healing response which results in the formation of capillaries at the site of the implant. Moreover, the angiogenesis action resulting by the location of the agents within the lumens over time will further revascularize the myocardium. As such, these implants may provide less of a short term improvement to vascularization, but instead will lead to a long term improvement.

As should be appreciated from the foregoing whether the system 20 makes use of non-resorbable or resorbable agents is of little relevance from the standpoint of increased blood flow to the myocardium tissue and capillaries contiguous with the lumens so long as the agents are constructed suitably.

Figure 16:
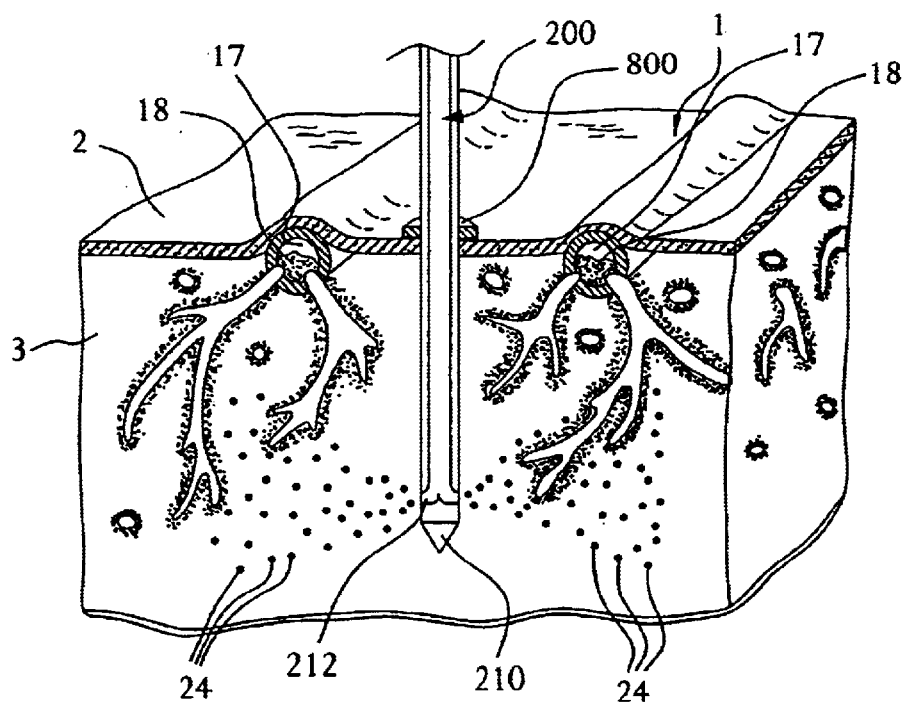
FIG. 16 is a side sectional view of one embodiment of a delivery instrument of a targeted tissue treatment, e.g., a myocardial revascularization, system of this invention being used to pierce the epicardium, create a channel in the myocardium, and deliver the flowable agent(s) into myocardium whose vasculature has been reduced over time by atherosclerosis.

FIG. 16 is an illustration of a portion of the heart of a living human being, partially in section, showing the embodiment of a jet injector delivery instrument 200 (described earlier and shown in FIG. 7) shown used to deliver the flowable agent(s) of this invention into the myocardium 3 via the epicardium 2. The coronary vessels 17 perfusing the myocardium are at least partially obstructed by atherosclerotic material 18. As previously described, the device 200 utilizes a pressurized stream to distribute the flowable agents into targeted tissues. In this particular embodiment, microparticles or microspheres like those described earlier and shown in FIG. 15 are implanted or injected into a portion of myocardium in the form of a micro dispersion. The velocity of the microparticles when exiting the instrument may be of sufficient velocity to penetrate the myocardium but not penetrate a coronary vessel if encountered. As previously discussed the instrument 200 may be stabilized on the surface of the heart and the depth of the instrument in the myocardium may also be controlled. One embodiment of a stabilizing and depth control member 800 is shown as part of the instrument 200.

Figure 17:
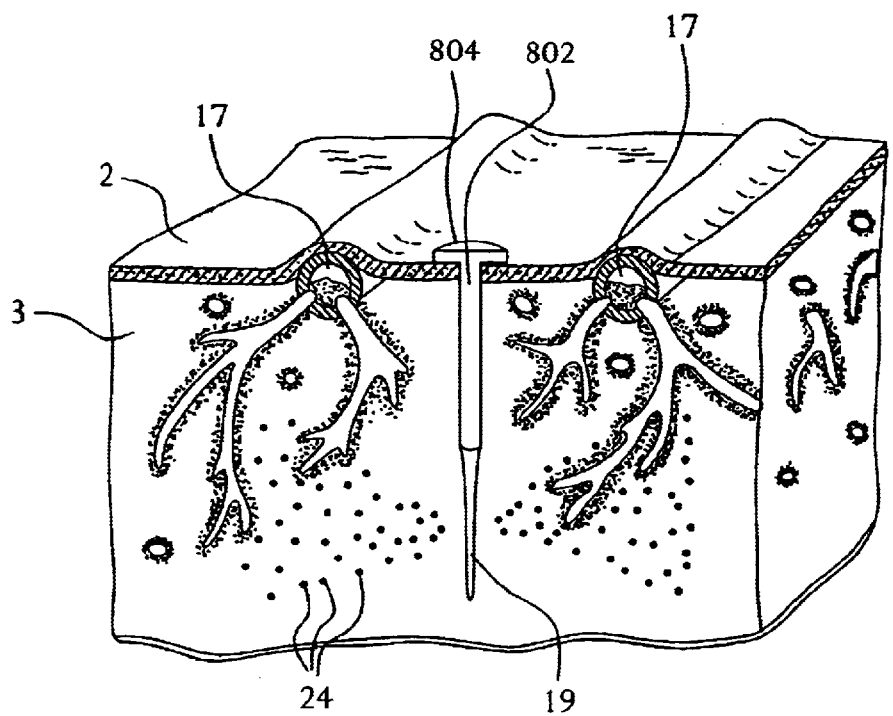
FIG. 17 is an illustration, like that of FIG. 16, but showing the myocardium immediately after the introduction of the small particles of the flowable agent(s) into the channel in the myocardium followed by the placement of an insert into the channel to increase the vasculature of by the myocardium by the creation of new vessels, e.g., capillaries, in the myocardium.

Referring to FIG. 17, after the instrument 200 shown in FIG. 16 is removed, the microdistribution of microparticles 24 remain in the myocardium 3. The microparticles 24 are sufficiently implanted into the myocardium to resist movement. The combination of the microparticles and the injury created by the instrument 200 to deploy and disperse the particles may effect angiogenesis. Additionally a channel or lumen 19 remains in the myocardium area where the instrument was inserted. An insert or plug 802 may be placed in the channel 19 after the instrument 200 is removed. This action may assist in achieving hemostasis of the puncture. For this purpose, the insert or plug 802 may be formed of a hemostatic material, such as collagen or alginate, and may incorporate thrombogenic material, such as thrombin, to accelerate hemostasis of the channel. The insert or plug 802 may also have an enlarged proximal head portion 804 that may limit the depth of insertion depth of the insert or plug and may also serve to stabilize the insert or plug against the surface of the myocardium. The insert or plug 802 may also be formed of a material which will contribute to the improved revascularization such as those listed on Tables 3 and 4. The insert may also serve to maintain the patency of the channel or lumen. As such, a portion of the insert or plug can be perforated or include channels (see for example the inserts of the aforementioned copending application Ser. No. 08/958,788). The insert itself may also act to treat the surrounding tissue. For example, the insert or plug 802 may also comprise a biologically active ingredient or pharmaceutical ingredient as listed on Tables 1 and 2. Finally, the insert or plug 802 may also be useful in the selective ablation or improvement of electrical conduction pathways, or the selective ablation or improvement of the nerves of the tissue.

Figure 18:
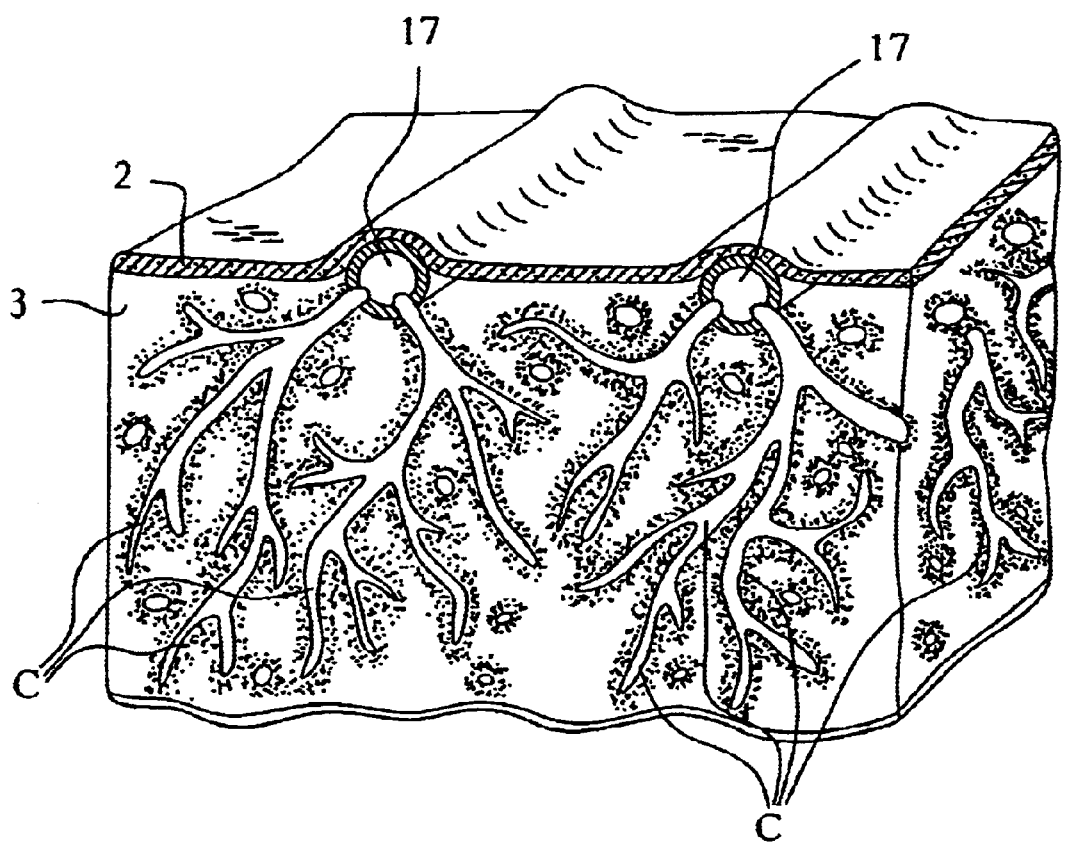
FIG. 18 is an illustration like that of 17, but showing the myocardium some time after treatment by the system of FIGS. 16 and 17 where the deployed particles and insert have stimulated angiogenesis to improve the blood flow in the contiguous portion of myocardium.

FIG. 18 shows the condition of the myocardium 3 after angiogenesis has occurred to create significant new vasculature, e.g., capillaries C. As can be seen at this time, the microparticles 24 and the insert 802 have been absorbed and the channel 19 formed by the instrument have healed. In addition and quite significantly, the microparticles, the insert, and any biologically active materials or pharmaceutical agents which may have also been implanted have induced the growth of the new vasculature (capillaries) C or otherwise improved the tissue.

Figure 19:
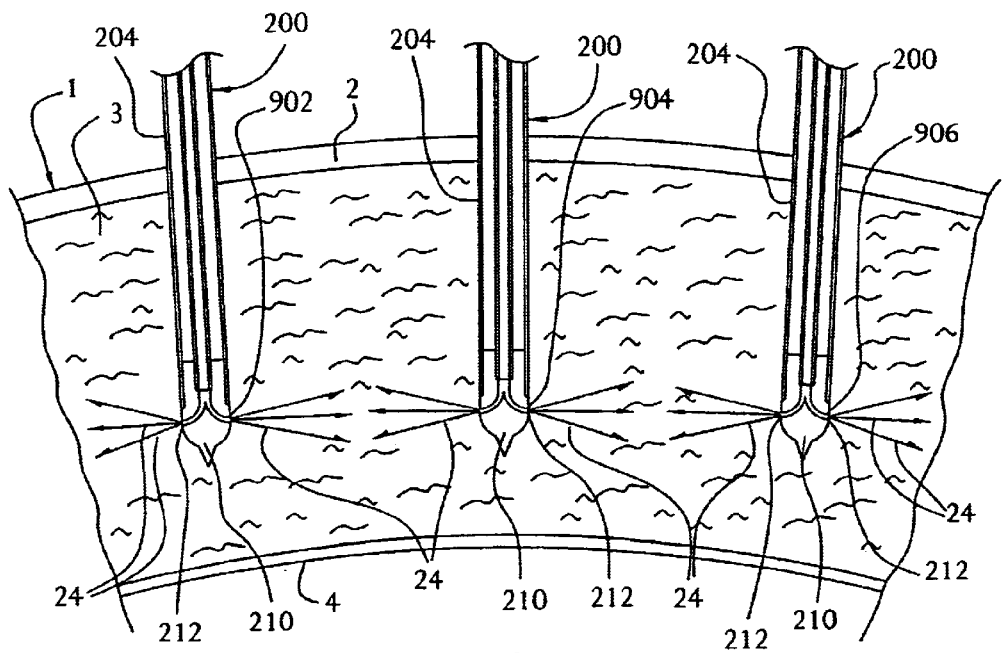
FIG. 19 is an illustration of a portion of the heart of a living being, shown partially in section, and showing a flowable treatment agent delivery system like that of FIG. 7 delivering the agent(s) at plural locations to result in the production of an intramyocardial channel for providing an enhanced blood supply to ischemic myocardial tissue.

FIG. 19 is an illustration of a portion of the heart 1 of a living being, shown partially in section and showing the embodiment of the delivery instrument 200 of FIG. 7 used to deliver the flowable agent(s) 24 into the myocardium in the form of pressurized streams of fluid. In this figure three instruments 200 are illustrated for introducing the flowable agents into the myocardium at three different locations 902, 904, and 906. While three delivery instruments 200 are illustrated extending into the myocardium together, the system 20 will typically only include a single delivery for delivering the agents to one site 902, 904 and 906 in the myocardium at a time. Therefore, it should be understood that FIG. 19 should be understood to depict the sequential delivery of the flowable agent(s) 24 into the myocardium 3 by a single delivery instrument 200.

At high pressures, the stream of flowable agent(s) 24 delivered to the myocardium may cause separation of the myocardial muscular fibers and may form a channel in the myocardium. If the delivery instrument is inserted into the myocardium at several locations at controlled distances between insertion points, the channels formed by the pressurized stream of fluid may be contiguous with one another, thus forming a long channel within the myocardium. Furthermore, a portion of the myocardium may be normally perfused with blood and an adjacent portion of the myocardium may be ischemic. If the instrument 200 is inserted in a plurality of locations at controlled distances between insertion points in the normally perfused myocardium and extending into and possibly through the ischemic myocardium, an intramyocardial channel (like that designated by reference number 908 in FIG. 20) from the normally perfused myocardium extending into the ischemic myocardium results. This channel is expected to remain patent, thereby resulting in immediate increased perfusion to the ischemic myocardium.

Regardless of the immediate patency of the channel 908, the combination of the mechanical injury produced by the creation of the channel and the flowable agents 24 may cause the creation of additional vasculature including and in addition to the formed channel, thereby resulting in increased perfusion of the portion of ischemic myocardium. Depending on the degree of ischemia and the area of ischemic myocardium, several channels may be formed in the area of the ischemic myocardium. The channels may or may not originate or terminate in a portion of normally perfused myocardium.

Regarding the pressurized stream of fluid used to create the channel 908, the instrument 200 may utilize multiple flowable agents 24 to create the channel and implant agents into the myocardium. For example, one flowable agent, e.g., saline mixed with contract medium, may be used to create the channel and a second flowable agent, e.g., saline with bFGF coated microspheres and VEGF coated microspheres, may be implanted into the channel and at some significant distance into the myocardium surrounding the created channel. Additionally, the channel may be formed in communication with an existing coronary vessel to provide significant blood flow to the channel. The communication of existing vessel and channel may be effected by creating an opening in the existing vessel with the delivery of flowable agent in a pressurized stream from within the myocardium or from within the vessel.

Figure 20:
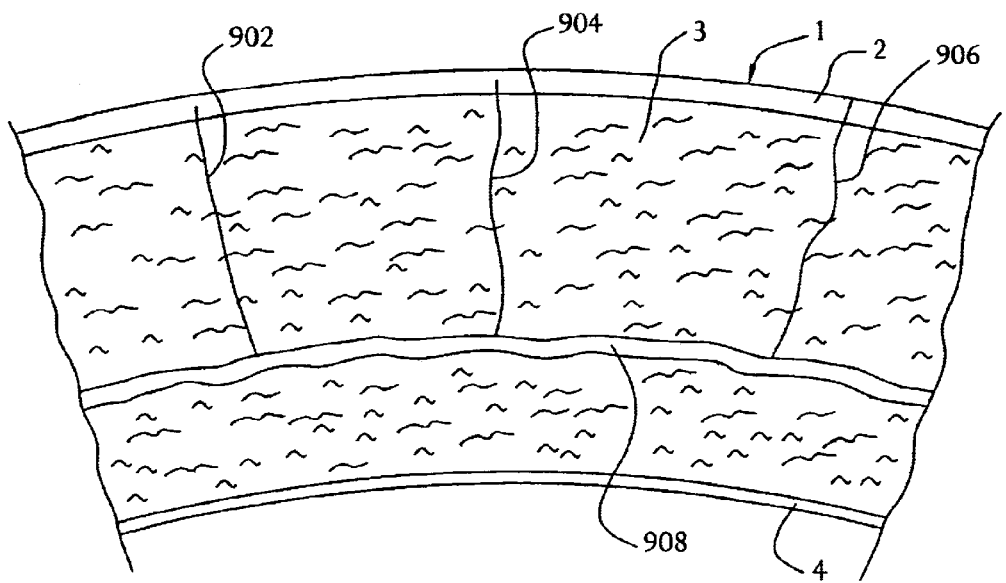
FIG. 20 is an illustration of the portion of the heart shown in FIG. 19 after the treatment procedure as depicted therein.

FIG. 20 is an illustration of a portion of the heart shown in FIG. 19, but after its treatment by the system of the subject invention. Thus, as can be seen, the channel 908 in the myocardium which was created by the delivery system of the subject invention is open and may extend between normally perfused myocardium and ischemic myocardium to provide immediate blood flow to the ischemic myocardium. In addition or alternatively the channel 908 may serve as a means whereby new blood vessels may grow, supplemented by the introduction of a flowable agent as previously described.

In order to prevent the flow of blood from the channel 908 through the instrument's entry sites 902, 904 and 906 into the myocardium, a hemostatic insert may be applied in each channel created by the instrument, like that described with reference to FIG. 17. Alternatively, an adhesive material, e.g., fibrin glue, may be applied to the surface of the myocardium at the delivery instrument insertion point or within the channel created by the instrument, to cause the original entry channels close down as shown in FIG. 20.

Figure 21:
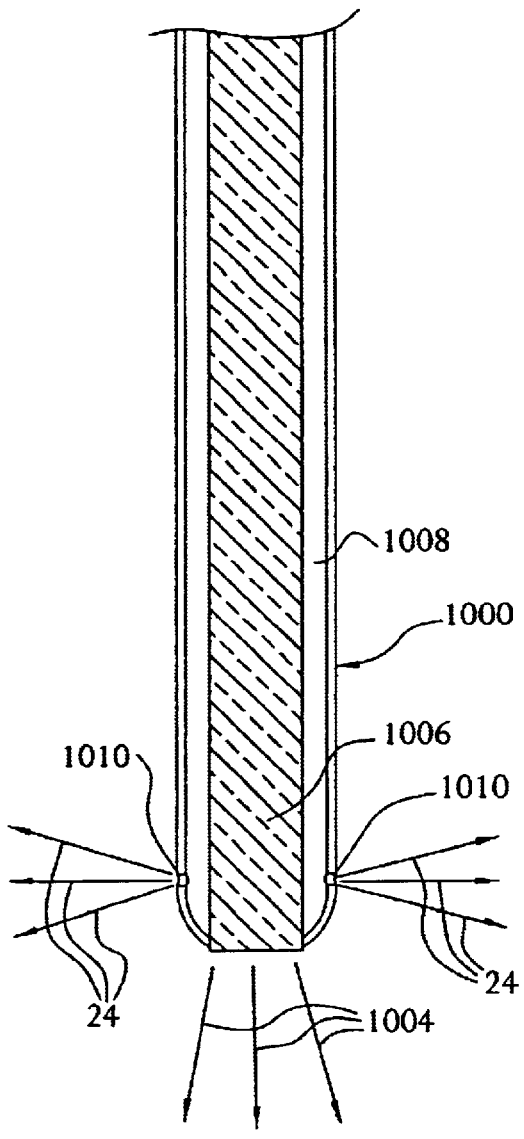
FIG. 21 is an enlarged sectional view of the distal or working end of yet another alternative delivery instrument of the targeted tissue treatment system of this invention.

FIG. 21 is an enlarged sectional view of the distal end portion of the treatment agent delivery instrument 1000 forming a portion of the tissue treatment system 20 of this invention. The delivery instrument 1000 incorporates an energy applicator, e.g., a laser (not shown), to provide energy denoted by the arrows designated by the reference numbers 1004 into the targeted tissue, e.g., the myocardium 3, to produce a channel therein and into which the flowable agent(s) 24 may be introduced. In particular, the laser beam 1004 from the laser is carried down the instrument 1000 via any suitable laser energy conductor, e.g., a light pipe or fiber optic cable 1006. An annular passageway 1008 is provided within the distal end portion of the instrument 1000 surrounding the laser energy conductor 1006. A plurality of exit ports 1010 are located at peripherally spaced locations at the distal end of the instrument adjacent the free end at which the laser energy conductor 1006 terminates and are in fluid communication with the passageway 1008. The passageway 1008 and the communicating ports 1010 serve as the means to enable the flowable agent(s) 24 to exit from the instrument in plural jets.

The instrument 1000 of FIG. 21 is inserted into the targeted tissue, e.g., the myocardium, by applying laser energy from the laser source through the conductor 1006 so that the laser beam 1004 penetrates into the tissue to form a channel into which the distal end of the instrument 1000 may be inserted. Once the instrument 1000 is within the channel in the tissue, the flowable agent(s) 24 may be introduced into the tissue by causing it to flow down the annular passageway 1008 and out through the ports 1010 in the form of pressurized jets. The combination of the application of the energy to create the channel plus the delivery of the flowable agent(s) 24 into the tissue contiguous with the channel is expected to result in increased beneficial effects to that tissue, such as the formation of new vasculature, denervation, and ablation of electrical conduction pathways.

Figure 22:
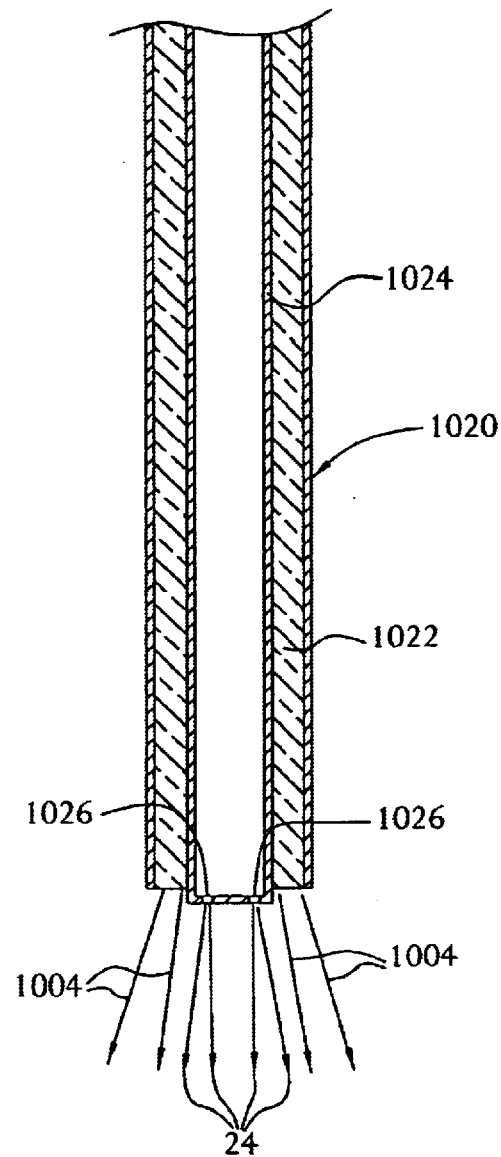
FIG. 22 is an enlarged sectional view of the distal or working end of still another alternative delivery instrument of the targeted tissue treatment system of this invention.

In FIG. 22, there is shown an alternative embodiment of a laser-energy based delivery instrument 1020. In this embodiment, the distal end of the instrument 1020 includes an annular laser energy conductor 22 for carrying the laser energy or beam 1004 down it from the laser energy source (not shown) so that the laser beam exits the instrument in a somewhat coaxial direction as shown. A central passageway 1024 is provided in the instrument located within the central opening in the annular laser conductor 1022. The passageway 1024 terminates at its distal end in a wall having plural outlet ports 1026. The ports 1026 are directed in a longitudinal or axial direction with respect to the instrument. It is through these ports 1026 that the flowable agent(s) 24 is ejected from the instrument 1020 in the form of pressurized jets as shown in FIG. 22.

It should be pointed out at this juncture that the instrument in FIGS. 21 and 22 can utilize RF energy or other electromagnetic energy to produce the channels in the targeted tissue in lieu of the laser beam described. In any case with the embodiment 1000 shown in FIG. 21, the flowable agent is ejected in a radial direction, whereas with the embodiment of 1020 of FIG. 22, the flowable agents are ejected in an axial direction.

It should also be pointed out that the tissue treatment systems of this invention may be used without the inclusion of particles in the flowable agent. In such a case a fluid, e.g., a liquid or gas, fluid without particles but which may contain one or more of biologically active or pharmaceutical agents, such as but not limited to the agents disclosed in Tables 1 and 2 is delivered into the targeted tissue. Furthermore, the system described herein for the treatment of cardiac tissue may also be used in other tissues in the body to effect similar beneficial treatment. For example, constriction of peripheral arteries often creates areas of ischemic tissue not unlike ischemic myocardium as a result of coronary artery disease. The system of this invention may be used in these or other tissues to deliver therapeutic agents to improve blood flow through the creation of new vasculature. Other beneficial effects on the targeted tissue which may be achieved by the subject invention are pain reduction resulting from denervation in the treated tissue and interruption of electrical conduction pathways in the treated tissue resulting from ablation or some other process.

Without further elaboration the foregoing will so fully illustrate our invention that others may, by applying current or future knowledge, adopt the same for use under various conditions of service.

What is claimed is:

1. A method of vascularizing cardiac tissue of a living being using an instrument extended through a portion of the living being to an entry situs located within a vessel, duct or lumen at or adjacent the cardiac tissue, said method comprising the steps of:

(a) providing a flowable agent comprising a fluid and plurality of small particles;

(b) introducing said flowable agent through said instrument at said entry situs; and (c) imparting a particle-moving force through said instrument to said flowable agent, said particle-moving force being generated external to the living being to cause said flowable agent to form at least one stream of said fluid and said particles for passing directly through the tissue of said vessel, duct or lumen and contiguous tissue to target cardiac tissue located remotely from said entry situs, whereupon at least said particles of said stream pass through said tissue of said vessel, duct or lumen and contiguous tissue under the impetus of said particle-moving force without any mechanical means carrying said particles through said contiguous tissue, to directly enter said target cardiac tissue.

2. The method of claim 1 wherein at least some portion of at least some of said particles is formed of a material to cause the formation of lumens in communication with the being's arterial system.

3. The method of claim 1 wherein the cardiac tissue comprises the myocardium and wherein said method additionally comprises the step of applying energy to said flowable agent, and directing said flowable agent into the myocardium to treat the cardiac tissue.

4. The method of claim 3 wherein the presence of said flowable agent in the myocardium produces channels therein.

5. The method of claim 1 additionally comprising the step of monitoring the cardiac cycle of the being and coordinating the introduction of said flowable agent with the cardiac cycle.

* * * * *